(12) United States Patent
Klun et al.

(10) Patent No.: US 8,729,211 B2
(45) Date of Patent: *May 20, 2014

(54) PERFLUOROPOLYETHER URETHANE ADDITIVES HAVING (METH)ACRYL GROUPS AND HARD COATS

(71) Applicant: 3M Innovative Properties Company, St. Paul, MN (US)

(72) Inventors: Thomas P. Klun, Lakeland, MN (US); Naiyong Jing, Woodbury, MN (US); Richard J. Pokorny, Maplewood, MN (US); Zai-Ming Qiu, Woodbury, MN (US); Mark J. Pellerite, Woodbury, MN (US); William D. Coggio, Westford, MA (US); Christopher B. Walker, Jr., St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/908,102

(22) Filed: Jun. 3, 2013

(65) Prior Publication Data

US 2013/0261280 A1    Oct. 3, 2013

Related U.S. Application Data

(60) Continuation of application No. 13/396,669, filed on Feb. 15, 2012, now Pat. No. 8,476,398, which is a division of application No. 12/718,481, filed on Mar. 5, 2010, now Pat. No. 8,147,966, which is a division of application No. 11/277,162, filed on Mar. 22, 2006, now Pat. No. 7,718,264, which is a continuation-in-part of application No. 11/087,413, filed on Mar. 23, 2005, now abandoned.

(51) Int. Cl.
*C08G 18/50* (2006.01)
*C08G 18/79* (2006.01)
*C08G 18/04* (2006.01)
*C08G 18/06* (2006.01)

(52) U.S. Cl.
USPC .................. 528/60; 528/70; 528/75; 528/76; 528/34

(58) Field of Classification Search
USPC .............................. 528/44, 60, 70, 75, 76, 34
See application file for complete search history.

(56) References Cited

U.S. PATENT DOCUMENTS

| 3,250,808 A | 5/1966 | Moore, Jr. et al. |
| 3,734,962 A | 5/1973 | Niederprum et al. |

(Continued)

FOREIGN PATENT DOCUMENTS

| EP | 0479029 | 4/1992 |
| EP | 0339880 | 12/1993 |

(Continued)

OTHER PUBLICATIONS

International Search Report PCT/US2006/010344; Jul. 31, 2006; 4 pgs.

(Continued)

*Primary Examiner* — Thao T. Tran
(74) *Attorney, Agent, or Firm* — Carolyn A. Fischer

(57) ABSTRACT

Fluorocarbon- and urethane-(meth)acryl-containing additives and hardcoats. The hardcoats are particularly useful as a surface layer on an optical device.

16 Claims, 1 Drawing Sheet

(56) References Cited

U.S. PATENT DOCUMENTS

| | | | |
|---|---|---|---|
| 4,085,137 A | 4/1978 | Mitsch et al. | |
| 4,262,072 A | 4/1981 | Wendling et al. | |
| 4,321,404 A | 3/1982 | Williams et al. | |
| 4,472,480 A | 9/1984 | Olson | |
| 4,614,667 A | 9/1986 | Larson et al. | |
| 4,654,233 A | 3/1987 | Grant et al. | |
| 4,818,801 A * | 4/1989 | Rice et al. | 526/247 |
| 4,855,184 A | 8/1989 | Klun et al. | |
| 4,920,190 A * | 4/1990 | Lina et al. | 526/288 |
| 4,968,116 A | 11/1990 | Hulme-Lowe et al. | |
| 5,002,978 A | 3/1991 | Goldenberg | |
| 5,148,511 A | 9/1992 | Savu et al. | |
| 5,216,097 A * | 6/1993 | Allewaert et al. | 526/243 |
| 5,239,026 A | 8/1993 | Babirad et al. | |
| 5,609,990 A | 3/1997 | Ha et al. | |
| 5,677,050 A | 10/1997 | Bilkadi et al. | |
| 5,822,489 A | 10/1998 | Hale | |
| 5,846,650 A | 12/1998 | Ko et al. | |
| 5,948,478 A | 9/1999 | Lenti et al. | |
| 5,962,611 A | 10/1999 | Meijs et al. | |
| 6,127,498 A | 10/2000 | Tonelli et al. | |
| 6,210,858 B1 | 4/2001 | Yasuda et al. | |
| 6,224,949 B1 | 5/2001 | Wright et al. | |
| 6,238,798 B1 | 5/2001 | Kang et al. | |
| 6,299,799 B1 | 10/2001 | Craig et al. | |
| 6,376,572 B1 | 4/2002 | Turri | |
| 6,596,363 B2 | 7/2003 | Hayashida et al. | |
| 6,660,338 B1 | 12/2003 | Hargreaves | |
| 6,673,887 B2 | 1/2004 | Yamaguchi et al. | |
| 6,800,378 B2 | 10/2004 | Hawa et al. | |
| 6,815,040 B2 | 11/2004 | Pellerite | |
| 6,906,115 B2 | 6/2005 | Hanazawa et al. | |
| 7,119,959 B2 | 10/2006 | Shoshi et al. | |
| 7,537,828 B2 | 5/2009 | Coggio | |
| 7,632,874 B2 | 12/2009 | Hayashida | |
| 7,718,264 B2 * | 5/2010 | Klun et al. | 428/423.1 |
| 8,015,970 B2 | 9/2011 | Klun | |
| 8,147,966 B2 | 4/2012 | Klun | |
| 8,383,694 B2 * | 2/2013 | Klun et al. | 522/97 |
| 8,415,014 B2 * | 4/2013 | Klun et al. | 428/423.1 |
| 8,476,398 B2 * | 7/2013 | Klun et al. | 528/69 |
| 8,530,054 B2 * | 9/2013 | Padiyath et al. | 428/421 |
| 2002/0001710 A1 | 1/2002 | Kang et al. | |
| 2002/0085284 A1 | 7/2002 | Nakamura et al. | |
| 2002/0111518 A1 | 8/2002 | Wang et al. | |
| 2002/0115820 A1 | 8/2002 | Wang et al. | |
| 2003/0012936 A1 | 1/2003 | Draheim et al. | |
| 2003/0151029 A1 | 8/2003 | Hsu et al. | |
| 2004/0077775 A1 | 4/2004 | Audenaert et al. | |
| 2004/0209084 A1 | 10/2004 | Yamaya et al. | |
| 2005/0053790 A1 | 3/2005 | Kato | |
| 2005/0072336 A1 | 4/2005 | Itoh et al. | |
| 2005/0106404 A1 | 5/2005 | Hayashida et al. | |
| 2005/0112319 A1 | 5/2005 | Itoh et al. | |
| 2005/0123741 A1 | 6/2005 | Hayashida et al. | |
| 2005/0136252 A1 | 6/2005 | Chisholm et al. | |
| 2005/0158504 A1 | 7/2005 | Itoh et al. | |
| 2005/0158558 A1 | 7/2005 | Hayashida et al. | |
| 2005/0182199 A1 | 8/2005 | Jing et al. | |
| 2005/0228152 A1 | 10/2005 | Starry et al. | |
| 2005/0288385 A1 | 12/2005 | Kondo et al. | |
| 2006/0057307 A1 | 3/2006 | Matsunaga et al. | |
| 2006/0084756 A1 | 4/2006 | Southwell et al. | |
| 2006/0105155 A1 | 5/2006 | Ikeyama et al. | |
| 2006/0216500 A1 | 9/2006 | Klun et al. | |
| 2007/0286993 A1 | 12/2007 | Radcliffe et al. | |
| 2007/0287093 A1 | 12/2007 | Jing et al. | |
| 2007/0292679 A1 | 12/2007 | Pellerite | |
| 2008/0124555 A1 | 5/2008 | Klun | |
| 2010/0055470 A1 | 3/2010 | Klun | |
| 2010/0160595 A1 | 6/2010 | Klun | |
| 2011/0086221 A1 | 4/2011 | Pokorny | |

FOREIGN PATENT DOCUMENTS

| | | |
|---|---|---|
| EP | 0379462 | 2/1995 |
| EP | 0433070 | 1/1996 |
| EP | 0870778 | 10/1998 |
| EP | 1057849 | 8/2003 |
| EP | 1411073 | 4/2004 |
| JP | 5-209030 | 8/1993 |
| JP | 5209030 | 8/1993 |
| JP | 10-110118 | 4/1998 |
| JP | 11-503768 | 3/1999 |
| JP | 11080312 | 3/1999 |
| JP | 11-213444 | 8/1999 |
| JP | 11-293159 | 10/1999 |
| JP | 2002 036457 | 2/2002 |
| JP | 2002-190136 | 7/2002 |
| JP | 2002-194031 | 7/2002 |
| JP | 2002 332313 | 11/2002 |
| JP | 2004-043671 | 2/2004 |
| JP | 2004 083877 | 3/2004 |
| JP | 2004-204096 | 7/2004 |
| JP | 2005-126453 | 5/2005 |
| JP | 2006-037024 | 2/2006 |
| WO | WO 96/23828 | 8/1996 |
| WO | WO 01/00701 | 1/2001 |
| WO | WO 0130873 | 5/2001 |
| WO | WO 03/002628 | 1/2003 |
| WO | WO 03/072625 | 9/2003 |
| WO | WO 03/099904 | 12/2003 |
| WO | WO 2004/044062 | 5/2004 |
| WO | WO 2005/049687 | 6/2005 |
| WO | WO 2005/063484 | 7/2005 |
| WO | WO 2005/103175 | 11/2005 |
| WO | WO 2005/113641 | 12/2005 |

OTHER PUBLICATIONS

Fluorolink Polymer Modifiers product data sheet from: Solvay Solexis, Sep. 6, 2004, 5 pages.

* cited by examiner

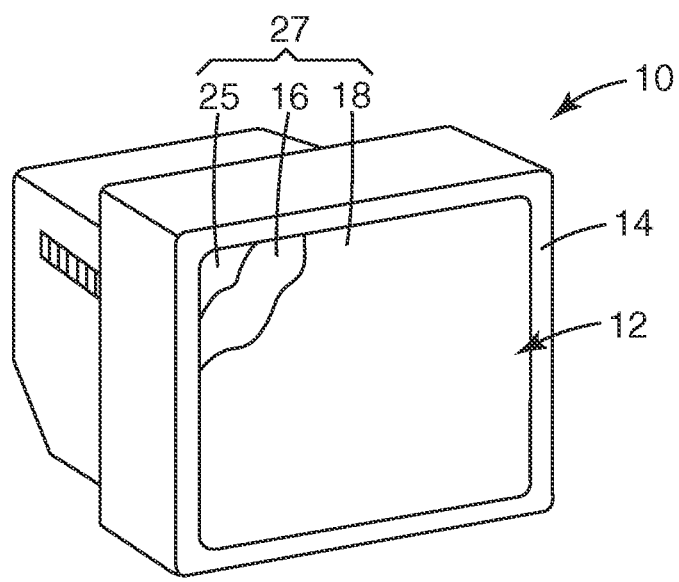

US 8,729,211 B2

PERFLUOROPOLYETHER URETHANE ADDITIVES HAVING (METH)ACRYL GROUPS AND HARD COATS

BACKGROUND OF THE INVENTION

Optical hard coats are applied to optical display surfaces to protect them from scratching and marking. Desirable product features in optical hard coats include durability to scratches and abrasions, and resistance to inks and stains.

Materials that have been used to date for surface protection include fluorinated polymers, or fluoropolymers. Fluoropolymers provide advantages over conventional hydrocarbon based materials in terms of high chemical inertness (solvent, acid, and base resistance), dirt and stain resistance (due to low surface energy), low moisture absorption, and resistance to weather and solar conditions.

Fluoropolymers have also been investigated that are crosslinked to a hydrocarbon-based hard coating formulation that improves hardness and interfacial adhesion to a substrate. For example, it is known that free-radically curable perfluoropolyethers provide good repellency to inks from pens and permanent markers when added to ceramer hard coat compositions, which comprise a plurality of colloidal inorganic oxide particles and a free-radically curable binder precursor, such as described in U.S. Pat. No. 6,238,798 to Kang, and assigned to 3M Innovative Properties Company of St. Paul, Minn.

Industry would find advantage in other fluoropolymer-based hard coatings, particularly those having improved properties.

SUMMARY OF THE INVENTION

In one aspect, the invention relates to fluorocarbon- and urethane-(meth)acryl-containing compositions suitable for use as additives in surface layer compositions for optical displays and other uses.

In one embodiment, the composition comprises a perfluoropolyether urethane having a monovalent perfluoropolyether moiety and a multi-(meth)acryl terminal group and is described in the detailed description below as Formula (1).

In another embodiment, the composition comprises a perfluoropolyether-substituted urethane acrylate having a monovalent perfluoropolyether moiety described in the detailed description below as Formula (3A) and more preferably as Formula (3B).

In a third embodiment, the composition comprises one or more perfluoropolyether urethanes having a monovalent perfluoropolyether moiety and a multi-(meth)acryl group of the Formula (4) as described further in the detailed description below.

In a fourth embodiment, the composition comprises one or more perfluoropolyether urethanes having a monovalent perfluoropolyether moiety and a multi-(meth)acryl group of the Formula (5) as described below in the detailed description.

In a fifth embodiment, the composition comprises one or more perfluoropolyether urethanes with multi-(meth)acryl groups of the Formula (6) as described below in the detailed description.

In other embodiments, polymerizable compositions, hardcoat composition, protective films and optical display are described having the perfluoropolyether urethanes of Formulas 1-6, a hydrocarbon hardcoat composition, and optionally a plurality of surface modified inorganic nanoparticles.

In other embodiments, articles such as optical displays and protective films are described that comprise an optical substrate having a surface layer comprising the reaction product of a mixture comprising i) at least one non-fluorinated crosslinking agent, and
ii) at least one perfluoropolyether urethane having a perfluoropolyether moiety and at least one free-radically reactive group; and a hardcoat layer comprising inorganic oxide particles disposed between the substrate and the surface layer.

The perfluoropolyether urethane additives can improve the compatibility of other fluorinated components such as free-radically reactive perfluoropolyether, fluoroalkyl, or fluoroalkylene group-containing components, such as for example perfluorobutyl-substituted acrylate components, as well as fluoroalkyl- or fluoroalkylene-substituted thiol or polythiol components.

In other embodiments, polymerizable coating compositions, hardcoat surface layers, optical displays, and protective films are described wherein the polymerizable composition comprises i) a hydrocarbon-based hardcoat composition (e.g. a non-fluorinated crosslinking agent); ii) at least one perfluoropolyether urethane having a perfluoropolyether moiety and at least one free-radically reactive group; iii) and at least one fluorinated compound having at least one moiety selected from fluoropolyether, fluoroalkyl, and fluoroalkylene linked to at least one free-radically reactive group with a non-urethane linking group.

In some aspects ii) comprises at least two (meth)acryl groups such as a terminal group having at least two (meth)acryl groups, with (meth)acrylates groups being preferred and acrylate groups being more preferred. Both ii) and iii) may comprise the perfluoropolyether moiety $F(CF(CF_3)CF_2O)_a CF(CF_3)$— wherein a ranges from 4 to 15.

Fluorinated compound iii) may be a mono- or multi-(meth)acrylate functional (e.g. perfluoropolyether) compound. The polymerizable composition may have a total weight percent fluorine ranging from 0.5 to 5 wt-%. The amount of i) may comprise at least about 75 wt-% of the mixture. Further, ii) and iii) may be present at a ratio ranging from 1:1 to 3:1. In one aspect, iii) has a ratio of fluorine atoms to non-fluorine atoms that is higher than ii). In another aspect, iii) has a lower molecular weight than ii).

Further, a particulate matting agent may be incorporated to impart anti-glare properties to the optical hard coating layer. The particulate matting agent can also prevent the reflectance decrease and uneven coloration caused by interference of the hard coat layer with the underlying substrate layer. In preferred embodiments, the (e.g. hardcoat) surface layers provide any one or combination of enhanced stain and ink repellency properties, adequate smoothness, and improved durability.

Other objects and advantages of the present invention will become apparent upon considering the following detailed description and appended claims, and upon reference to the accompanying drawings.

BRIEF DESCRIPTION OF THE DRAWINGS

FIG. 1 illustrates an article having a hard coated optical display formed in accordance with a preferred embodiment of the present invention.

DETAILED DESCRIPTION AND PREFERRED EMBODIMENTS

For the following defined terms, these definitions shall be applied, unless a different definition is given in the claims or elsewhere in the specification.

The term "(meth)acryl" refers to functional groups including acrylates, methacrylates, acrylamides, methacrylamides, alpha-fluoroacrylates, thioacrylates and thio-methacrylates. A preferred (meth)acryl group is acrylate.

The term "monovalent perfluoropolyether moiety" refers to a perfluoropolyether chain having one end terminated by a perfluoroalkyl group.

The term "ceramer" is a composition having inorganic oxide particles, e.g. silica, of nanometer dimensions dispersed in a binder matrix. The phrase "ceramer composition" is meant to indicate a ceramer formulation in accordance with the present invention that has not been at least partially cured with radiation energy, and thus is a flowing, coatable liquid. The phrase "ceramer composite" or "coating layer" is meant to indicate a ceramer formulation in accordance with the present invention that has been at least partially cured with radiation energy, so that it is a substantially non-flowing solid. Additionally, the phrase "free-radically polymerizable" refers to the ability of monomers, oligomers, polymers or the like to participate in crosslinking reactions upon exposure to a suitable source of free radicals.

The term "polymer" will be understood to include polymers, copolymers (e.g. polymers using two or more different monomers), oligomers and combinations thereof, as well as polymers, oligomers, or copolymers that can be formed in a miscible blend.

Unless otherwise noted, "HFPO—" refers to the end group $F(CF(CF_3)CF_2O)_aCF(CF_3)$— of the methyl ester $F(CF(CF_3)CF_2O)_aCF(CF_3)C(O)OCH_3$, wherein "a" averages 2 to 15. In some embodiments, a averages between 3 and 10 or a averages between 5 and 8. Such species generally exist as a distribution or mixture of oligomers with a range of values for a, so that the average value of a may be non-integer. In one embodiment a averages 6.2. This methyl ester has an average molecular weight of 1,211 g/mol, and can be prepared according to the method reported in U.S. Pat. No. 3,250,808 (Moore et al.), the disclosure of which is incorporated herein by reference, with purification by fractional distillation. The recitation of numerical ranges by endpoints includes all numbers subsumed within the range (e.g. the range 1 to 10 includes 1, 1.5, 3.33, and 10).

As used in this specification and the appended claims, the singular forms "a", "an", and "the" include plural referents unless the content clearly indicates otherwise. Thus, for example, reference to a composition containing "a compound" includes a mixture of two or more compounds. As used in this specification and the appended claims, the term "or" is generally employed in its sense including "and/or" unless the content clearly dictates otherwise.

Unless otherwise indicated, all numbers expressing quantities of ingredients, measurements of properties such as contact angle, and so like as used in the specification and claims understood to be modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings of the present invention. At the very least, and not as an attempt to limit the application of the doctrine of equivalents to the scope of the claims, each numerical parameter should be at least be construed in light of the number of reported significant digits and by applying ordinary rounding techniques. Notwithstanding that the numerical ranges and parameters set forth in the broad scope of the invention are approximations, the numerical values set forth in the specific examples are reported as accurately as possible. Any numerical value, however, inherently contains certain errors necessarily resulting from the standard deviations found in their respective testing measurements.

The term "optical display", or "display panel", can refer to any conventional optical displays, including but not limited to multi-character multi-line displays such as liquid crystal displays ("LCDs"), plasma displays, front and rear projection displays, cathode ray tubes ("CRTs"), and signage, as well as single-character or binary displays such as light emitting diodes ("LEDs"), signal lamps, and switches. The exposed surface of such display panels may be referred to as a "lens." The invention is particularly useful for displays having a viewing surface that is susceptible to being touched or contacted by ink pens, markers and other marking devices, wiping cloths, paper items and the like.

The protective coatings of the invention can be employed in a variety of portable and non-portable information display articles. These articles include PDAs, cell phones (including combination PDA/cell phones), LCD televisions (direct lit and edge lit), touch sensitive screens, wrist watches, car navigation systems, global positioning systems, depth finders, calculators, electronic books, CD and DVD players, projection television screens, computer monitors, notebook computer displays, instrument gauges, instrument panel covers, signage such as graphic displays and the like. The viewing surfaces can have any conventional size and shape and can be planar or non-planar, although flat panel displays are preferred. The coating composition or coated film, can be employed on a variety of other articles as well such as for example camera lenses, eyeglass lenses, binocular lenses, mirrors, retroreflective sheeting, automobile windows, building windows, train windows, boat windows, aircraft windows, vehicle headlamps and taillights, display cases, road pavement markers (e.g. raised) and pavement marking tapes, overhead projectors, stereo cabinet doors, stereo covers, watch covers, as well as optical and magneto-optical recording disks, and the like.

A combination of low surface energy (e.g. anti-soiling, stain resistant, oil and/or water repellency) and durability (e.g. abrasion resistance) is desired for the coating layer for these displays while maintaining optical clarity. The hard coating layer functions to decrease glare loss while improving durability and optical clarity.

The surface energy can be characterized by various methods such as contact angle and ink repellency, as determined by the test methods described in the Examples. In this application, "stain repellent" refers to a surface treatment exhibiting a static contact angle with water of at least 70 degrees. More preferably, the contact angle is at least 80 degrees and most preferably at least 90 degrees. Alternatively, or in addition thereto, the advancing contact angle with hexadecane is at least 50 degrees and more preferably at least 60 degrees. Low surface energy results in anti-soiling and stain repellent properties as well as rendering the exposed surface easy to clean.

Another indicator of low surface energy relates to the extent to which ink from a pen or marker beads up when applied to the exposed surface. The surface layer and articles exhibit "ink repellency" when ink from pens and markers beads up into discrete droplets and can be easily removed by wiping the exposed surface with tissues or paper towels, such as tissues available from the Kimberly Clark Corporation, Roswell, Ga. under the trade designation "SURPASS FACIAL TISSUE." Durability can be defined in terms of results from a modified oscillating sand test (Method ASTM F 735-94) carried out at 300 rpm for 15 minutes as described in the Test Methods of this application. Preferably, a durable coating exhibits an ink repellency loss value of 65 mm (75% loss) or less, more preferably 40 mm (45% loss) or less, most preferably 0 mm (no loss) of ink repellency (IR) in this test.

Coatings appropriate for use as optical hard coatings must be substantially free of visual defects. Visual defects that may be observed include but are not limited to pock marks, fisheyes, mottle, lumps or substantial waviness, or other visual indicators known to one of ordinary skill in the art in the optics and coating fields. Thus, a "rough" surface as described in the Experimental has one or more of these characteristics, and may be indicative of a coating material in which one or more components of the composition are incompatible with each other. Conversely, a substantially smooth coating, characterized below as "smooth" for the purpose of the present invention, presumes to have a coating composition in which the various components, in the reacted final state, form a coating in which the components are compatible or have been modified to be compatible with one another and further has little, if any, of the characteristics of a "rough" surface.

Additionally, the surface layer preferably exhibits an initial haze of less than 2% and/or an initial transmission of at least 90%.

Referring now to FIG. 1, a perspective view of an article (here a computer monitor 10) is illustrated as having an optical display 12 coupled within a housing 14. The optical display 12 is a substantially transparent material having optically enhancing properties through which a user can view text, graphics, or other displayed information. The optical display 12 includes hard coating layer 18 applied to an optical substrate 16. The thickness of the hardcoat layer is typically at least 0.5 microns, preferably at least 1 micron, and more preferably at least 2 microns. The thickness of the hardcoat layer is generally no greater than 25 microns. Preferably the thickness ranges from 3 microns to 5 microns.

In another embodiment (not shown), the hardcoat layer described herein (i.e. comprising at least one fluorocarbon- and urethane-(meth)acryl-containing additive and at least one non-fluorinated crosslinking agent) may be provided as a surface layer having an additional hard coat layer underlying the hardcoat surface layer. In this embodiment, the surface layer preferably has a thickness ranging from about 10 to 200 nanometers.

Various permanent and removable grade adhesive compositions may be coated on the opposite side of the substrate 16 (i.e. to that of the hardcoat 16) so the article can be easily mounted to a display surface. Suitable adhesive compositions include (e.g. hydrogenated) block copolymers such as those commercially available from Kraton Polymers of Westhollow, Tex. under the trade designation "Kraton G-1657", as well as other (e.g. similar) thermoplastic rubbers. Other exemplary adhesives include acrylic-based, urethane-based, silicone-based, and epoxy-based adhesives. Preferred adhesives are of sufficient optical quality and light stability such that the adhesive does not yellow with time or upon weather exposure so as to degrade the viewing quality of the optical display. The adhesive can be applied using a variety of known coating techniques such as transfer coating, knife coating, spin coating, die coating and the like. Exemplary adhesives are described in U.S. Pat. No. 7,351,470. Several of such adhesives are commercially available from 3M Company, St. Paul, Minn. under the trade designations 8141, 8142, and 8161.

The substrate layer 16 may consist of any of a wide variety of non-polymeric materials, such as glass, or polymeric materials, such as polyethylene terephthalate (PET), bisphenol A polycarbonate, cellulose triacetate, poly(methyl methacrylate), and biaxially oriented polypropylene which are commonly used in various optical devices. The substrate may also comprise or consist of polyamides, polyimides, phenolic resins, polystyrene, styrene-acrylonitrile copolymers, epoxies, and the like. Typically the substrate will be chosen based in part on the desired optical and mechanical properties for the intended use. Such mechanical properties typically will include flexibility, dimensional stability and impact resistance. The substrate thickness typically also will depend on the intended use. For most applications, substrate thicknesses of less than about 0.5 mm are preferred, and more preferably about 0.02 to about 0.2 mm. Self-supporting polymeric films are preferred. The polymeric material can be formed into a film using conventional filmmaking techniques such as by extrusion and optional uniaxial or biaxial orientation of the extruded film. The substrate can be treated to improve adhesion between the substrate and the hardcoat layer, e.g., chemical treatment, corona treatment such as air or nitrogen corona, plasma, flame, or actinic radiation. If desired, an optional tie layer or primer can be applied to the substrate and/or hardcoat layer to increase the interlayer adhesion.

In the case of display panels, the substrate is light transmissive, meaning light can be transmitted through the substrate 16 such that the display can be viewed. Both transparent (e.g. gloss) and matte light transmissive substrates 16 are employed in display panels 10. Matte substrates 16 typically have lower transmission and higher haze values than typical gloss films. The matte films exhibit this property typically due to the presence of micron size dispersed inorganic fillers such as silica that diffuse light. Exemplary matte films are commercially available from U.S.A. Kimoto Tech, Cedartown, Ga. under the trade designation "N4D2A". In case of transparent substrates, hardcoat coated transparent substrates, as well as the display articles comprised of transparent substrates, the haze value is preferably less than 5%, more preferably less than 2% and even more preferably less than 1%. Alternatively or in addition thereto, the transmission is preferably greater than about 90%.

Various light transmissive optical films are known including but not limited to, multilayer optical films, microstructured films such as retroreflective sheeting and brightness enhancing films, (e.g. reflective or absorbing) polarizing films, diffusive films, as well as (e.g. biaxial) retarder films and compensator films such as described in U.S. Pat. No. 7,099,083.

As described is U.S. Pat. No. 6,991,695, multilayer optical films provide desirable transmission and/or reflection properties at least partially by an arrangement of microlayers of differing refractive index. The microlayers have different refractive index characteristics so that some light is reflected at interfaces between adjacent microlayers. The microlayers are sufficiently thin so that light reflected at a plurality of the interfaces undergoes constructive or destructive interference in order to give the film body the desired reflective or transmissive properties. For optical films designed to reflect light at ultraviolet, visible, or near-infrared wavelengths, each microlayer generally has an optical thickness (i.e., a physical thickness multiplied by refractive index) of less than about 1 µm. However, thicker layers can also be included, such as skin layers at the outer surfaces of the film, or protective boundary layers disposed within the film that separate packets of microlayers. Multilayer optical film bodies can also comprise one or more thick adhesive layers to bond two or more sheets of multilayer optical film in a laminate.

Further details of suitable multilayer optical films and related constructions can be found in U.S. Pat. No. 5,882,774 (Jonza et al.), and PCT Publications WO 95/17303 (Ouderkirk et al.) and WO 99/39224 (Ouderkirk et al.). Polymeric multilayer optical films and film bodies can comprise additional layers and coatings selected for their optical, mechanical, and/or chemical properties. See U.S. Pat. No. 6,368,699 (Gilbert et al.). The polymeric films and film bodies can also comprise inorganic layers, such as metal or metal oxide coatings or layers. The composition of the hard coating layer 18, prior to application and curing to the optical substrate 16, is formed from a mixture of a conventional hydrocarbon-based, and more preferably acrylate-based, hard coat composition and a fluorocarbon- and urethane-acrylate-containing additive. Preferred fluorocarbon- and urethane-acrylate-containing additive compositions are described in Formulas (1), (3A), (4), (5) and (6) below. Methods for forming the hard coating compositions for each of the preferred embodiments are described below in the experimental section.

In one preferred embodiment of the present invention, the fluorocarbon- and urethane-acrylate-containing additive is a perfluoropolyether urethane having a monovalent perfluoropolyether moiety and a multi-acrylate terminal group combined with a conventional hydrocarbon-based (more preferably acrylate-based) hard coat material. The perfluoropolyether urethane having a monovalent perfluoropolyether moiety and a multi-acrylate terminal group is added at between about 0.01% and 10%, and more preferably between about 0.1% and 1%, of the total solids of the hard coat composition. The additive is of the Formula (1):

$$R_i\text{—(NHC(O)XQR}_f)_m\text{,—(NHC(O)OQ(A)}_p)_n \tag{1}$$

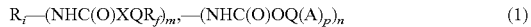

wherein $R_i$ is a residue of a multi-isocyanate; X is O, S or NR, where R is H or lower alkyl of 1 to 4 carbon atoms; $R_f$ is a monovalent perfluoropolyether moiety composed of groups comprising the formula $F(R_{fc}O)_x C_d F_{2d}\text{—}$, wherein each $R_{fc}$ independently represents a fluorinated alkylene group having from 1 to 6 carbon atoms, each x independently represents an integer greater than or equal to 2, and wherein d is an integer from 1 to 6; Q is independently a connecting group of valency at least 2; A is a (meth)acryl functional group —XC(O)C($R_2$)=CH$_2$, where $R_2$ is a lower alkyl of 1 to 4 carbon atoms or H or F; m is at least 1; n is at least 1; p is 2 to 6, m+n is 2 to 10, and in which each unit referred to by the subscripts m and n is attached to an $R_i$ unit.

Q can be a straight or branched chain or cycle-containing connecting group. Q can include a covalent bond, an alkylene, an arylene, an aralkylene, an alkarylene. Q can optionally include heteroatoms such as O, N, and S, and combinations thereof. Q can also optionally include a heteroatom-containing functional group such as carbonyl or sulfonyl, and combinations thereof.

By their method of synthesis, these materials are necessarily mixtures. If the mole fraction of isocyanate groups is arbitrarily given a value of 1.0, then the total mole fraction of m and n units used in making materials of Formula (1) is 1.0 or greater. The mole fractions of m:n ranges from 0.95:0.05 to 0.05:0.95. Preferably, the mole fractions of m:n are from 0.50:0.50 to 0.05:0.95. More preferably, the mole fractions of m:n are from 0.25:0.75 to 0.05:0.95 and most preferably, the mole fractions of m:n are from 0.25:0.75 to 0.10:0.95. In the instances the mole fractions of m:n total more than one, such as 0.15:0.90, the m unit is reacted onto the isocyanate first, and a slight excess (0.05 mole fraction) of the n units are used.

In a formulation, for instance, in which 0.15 mole fractions of m and 0.85 mole fraction of n units are introduced, a distribution of products is formed in which some fraction of products formed contain no m units. There will, however, be present in this product distribution, materials of Formula (1).

Numerous diisocyanates (di-functional isocyanates), modified diisocyanate materials, and higher functional isocyanates may be used as $R_i$ in the present invention as the residue of multi-isocyanate and still fall within the spirit of the present invention. Most preferably, multifunctional materials based on hexamethylene diisocyanate ("HDI") are utilized. One commercially available derivative of HDI is Desmodur™ N100, available from Bayer Polymers LLC of Pittsburgh, Pa.

Further, other diisocyanates such as toluene diisocyanate ("TDI") or isophorone diisocyanate ("IPDI") may also be utilized as $R_i$ in the present invention. Non-limiting examples of aliphatic and aromatic isocyanate materials, for example, that may be used include Desmodur™ 3300, Desmodur™ TPLS2294, and Desmodur™ N 3600, all obtained from Bayer Polymers LLC of Pittsburgh, Pa.

Materials used to make the additive of Formula (1) may be described by the Formula: $HOQ(A)_p$, which are exemplified by, for instance, 1,3-glycerol dimethacrylate, available from Echo Resins Inc. of Versailles, Mo.; and pentaerythritol triacrylate, available as SR444C from Sartomer of Exton, Pa.

Typically, the additive compositions of this preferred embodiment are made by first reacting the polyisocyanate with the perfluoropolyether-containing alcohol, thiol, or amine, followed by reaction with the hydroxyl functional multiacrylate, usually in a non-hydroxylic solvent and in the presence of a catalyst such as an organotin compound. Alternatively, the additives of this preferred embodiment are made by reacting the polyisocyanate with the hydroxyl functional multiacrylate, followed by reaction with the perfluoropolyether-containing alcohol, thiol, or amine, usually in a non-hydroxylic solvent and in the presence of a catalyst such as an organotin compound. In addition, the additives could be made by reacting all three components simultaneously, usually in a non-hydroxylic solvent and in the presence of a catalyst such as an organotin compound.

One representative structure (2) of perfluoropolyether urethanes with multi-acrylate terminal groups of Formula (1) is shown below as:

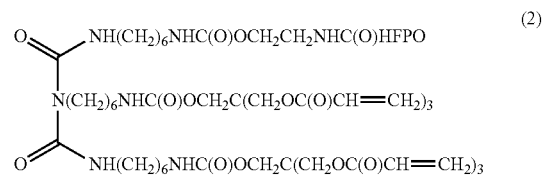

(2)

which is the reaction product of the biuret of HDI with one equivalent of HFPO oligomer amidol (F(CF(CF$_3$)CF$_2$O)$_a$CF(CF$_3$)C(O)NHCH$_2$CH$_2$OH) and further with two equivalents of pentaerythritol triacrylate, wherein "a" averages 2 to 15. In some embodiments, a averages between 3 and 10 or a averages between 5 and 8.

In another embodiment, the additive composition is of the Formula (3A):

$$R_f\text{-Q-(XC(O)NHQOC(O)C(R)}=\text{CH}_2)_f \tag{3A}$$

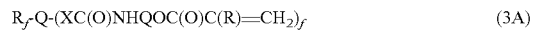

where $R_f$, Q and X are the same as previously described with reference to Formula (1) and f is 1-5.

One preferred perfluoropolyether-substituted urethane (meth)acrylate that meets the description of Formula (3A) is described more specifically in Formula (3B):

$$HFPO\text{-Q-(XC(O)NHQOC(O)C(R)}=\text{CH}_2)_f \tag{3B}$$

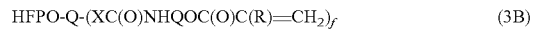

Two preferred HFPO-substituted urethane acrylates that can be utilized include HFPO—C(O)NHC$_2$H$_4$OC(O)

NHC₂H₄OC(O)C(CH₃)=CH₂ and HFPO— C(O)NHC(C₂H₅)(CH₂OC(O)NHC₂H₄OC(O)C(CH₃)=CH₂)₂.

In another embodiment, the additive composition is of the Formula (4):

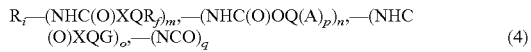

$$R_i—(NHC(O)XQR_f)_m,—(NHC(O)OQ(A)_p)_n,—(NHC(O)XQG)_o,—(NCO)_q \quad (4)$$

wherein $R_i$ is a residue of a multi-isocyanate; X, $R_f$ and Q are the same as previously described with reference to Formula (1). A is a (meth)acryl functional group —XC(O)C(R₂)=CH₂, where R₂ is a lower alkyl of 1 to 4 carbon atoms or H or F; G is selected from the group consisting of an alkyl, an aryl, an alkaryl and an aralkyl. G optionally contains heteroatoms such as O, N, and S, and combinations thereof. G also optionally has heteroatom-containing functional groups such as carbonyl, sulfonyl, and combinations thereof. Further, G may have a combination of heteroatoms and heteroatom-containing functional groups. G optionally contains pendant or terminal reactive groups. The reactive group may include (meth)acryl groups, vinyl groups, allyl groups and —Si(OR₃)₃ groups, where R₃ is a lower alkyl of 1 to 4 carbon atoms. G also optionally has fluoroalkyl or perfluoroalkyl groups. In Formula (4), m is at least 1; n is at least 1; o is at least 1; p is 2 to 6; and q is 0 or greater.

(m+n+o+q)=$N_{NCO}$, the number of isocyanate groups originally appended to $R_i$; and the quantity (m+n+o)/$N_{NCO}$ is greater than or equal to 0.67, and in which each unit referred to by the subscripts m, n, o, and q is attached to an $R_i$ unit. Preferably $R_{fc}$ is —CF(CF₃)CF₂—.

The monoalcohol, monothiol or monoamine HXQG used in making materials of Formula (4) may include materials such as C₄F₉SO₂N(CH₃)CH₂CH₂OH, H₂NCH₂CH₂CH₂(SiOCH₃)₃, HSCH₂CH₂CH₂Si(OCH₃)₃, and HEA (hydroxyethylacrylate).

In another embodiment, the additive composition is of the Formula (5):

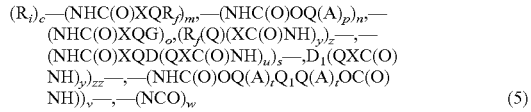

$$(R_i)_c—(NHC(O)XQR_f)_m,—(NHC(O)OQ(A)_p)_n,—(NHC(O)XQG)_o,—(R_f(Q)(XC(O)NH)_y)_z,—(NHC(O)XQD(QXC(O)NH)_u)_s,—,D_1(QXC(O)NH)_y)_{zz},—(NHC(O)OQ(A)_tQ_1Q(A)_tOC(O)NH))_v,—(NCO)_w \quad (5)$$

wherein $R_i$ is the residue of a multi-isocyanate; c is 1 to 50; X, $R_f$ and Q are the same as previously described with reference to Formula (1). A and G are the same as previously described with reference to Formula 4. D is alkylene, arylene, alkarylene, fluoroalkylene, perfluoroalkylene or aralkylene; and optionally contains heteroatoms such as O, N, and S. $D_1$ is alkyl, aryl, alkaryl, fluoroalkyl, perfluoroalkyl or aralkyl; optionally containing heteroatoms such as O, N, and S. $Q_1$ is a connecting group defined in the same way as Q. In Formula 5, m or z is at least 1; n or v is at least 1; y is independently 2 or greater; o, s, v, w, z and zz are 0 or greater. The sum of s, v, z and zz is at least one. Therefore, at least one of these groups is present.

(m+n+o+[(u+1)s]+2v+w+yz+y(zz))=$cN_{NCO}$ the number of isocyanate groups originally appended to $R_i$. The quantity (m+n+o+([(u+1)s]+2v+yz+y(zz))/($cN_{NCO}$) is greater than or equal to least 0.75. In Formula 5, p is 2 to 6; t is 1 to 6; and u is independently 1 to 3; in which each unit referred to by the subscripts m, n, o, s, v, w, z and zz is attached to an $R_i$ unit. Preferably $R_{fc}$ is —CF(CF₃)CF₂—.

In this embodiment, when added to the conventional hydrocarbon-based hard coating material, care must be taken in choosing the ratios and amounts of reactive components to avoid highly crosslinked urethane polymer gels. For instance, if a trifunctional isocyanate is to be used with a multifunctional alcohol, the amount of multifunctional alcohol should be limited to avoid forming a crosslinked network. For higher numbers of c for $(R_i)_c$ groups, it is preferred that the formulation be based primarily on diols and diisocyanates.

The materials used to make the additive of Formula (5) include those of the formula $R_f(Q)(XH)_y$, which is exemplified by HFPO—C(O)NHCH₂CH₂CH₂N(CH₂CH₂OH)₂.

The materials used to make the additive of Formula (5) include those of the formula: HXQDQXH, which is exemplified by hydrocarbon polyols such as HO(CH₂)₁₀OH and fluorochemical diols such as HOCH₂(CF₂)₄—CH₂OH.

The materials used to make the additive of Formula (5) may include those of the formula D(QXH)$_y$)$_{zz}$, which is exemplified by fluorochemical diols C₄F₉SO₂N(CH₂CH₂OH)₂.

The materials used to make the additive of Formula (5) may also include those of the formula HOQ(A)$_t$Q₁Q(A)$_t$OH, which is exemplified by hydantoin hexaacrylate (HHA), prepared as described in Example 1 of U.S. Pat. No. 4,262,072 to Wendling et al, and CH₂=C(CH₃)C(O)OCH₂CH(OH)CH₂O(CH₂)₄OCH₂CH(OH)CH₂OC(O)C(CH₃)=CH₂.

In still another embodiment the additive composition is of the Formula (6):

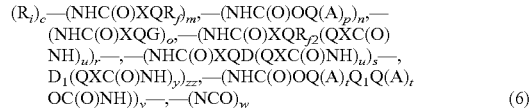

$$(R_i)_c—(NHC(O)XQR_f)_m,—(NHC(O)OQ(A)_p)_n,—(NHC(O)XQG)_o,—(NHC(O)XQR_{f2}(QXC(O)NH)_u)_r,—(NHC(O)XQD(QXC(O)NH)_u)_s,—,D_1(QXC(O)NH)_y)_{zz},—(NHC(O)OQ(A)_tQ_1Q(A)_tOC(O)NH))_v,—(NCO)_w \quad (6)$$

wherein $R_i$ is the residue of a multi-isocyanate; c is 1 to 50; X, $R_f$, Q, Q₁, A, G, D, and $D_1$ are the same as previously described with reference to Formula (5). $R_{f2}$ is a multi-valent fluoropolyether moiety, $R_{f2}$ is composed of groups comprising the formula Y (($R_{fc1}$O)$_x$C$_{d1}$F$_{2d1}$)$_b$ wherein each $R_{fc1}$ independently represents a fluorinated alkylene group having from 1 to 6 carbon atoms: each x independently represents an integer greater than or equal to 2, and d1 is an integer from 0 to 6. Y represents a polyvalent organic group or covalent bond having a valence of b, and b represents an integer greater than or equal to 2. In Formula (5), r is at least 1; n or v is at least 1; y is independently 2 or greater. Further, m, o, s, v, w and zz are 0 or greater.

(m+n+o+[(u+1)r]+[(u+1)s]+2v+w+y(zz))=$cN_{NCO}$ the number of isocyanate groups originally appended to R. The quantity (m+n+o+[(u+1)r]+[(u+1)s]+2v+y(zz))/($cN_{NCO}$) is greater than or equal to least 0.75.

In Formula (5), p is 2 to 6; t is 1 to 6; u is independently 1 to 3; in which each unit referred to by the subscripts m, n, o, r, s, v, w, and zz is attached to an $R_i$ unit. $R_{fc1}$ is preferably independently selected from —CF(CF₃)CF₂—, —CF₂CF₂CF₂—, and (—CH₂C(R)(CH₂OCH₂C$_d$F$_{2d+1}$)CH₂—)$_{aa}$ where aa is 2 or greater and d and R are defined above.

The materials used to make the additive of Formula (9) may also include those of the formula HXQR$_{f2}$QXH, which is exemplified by (H(OCH₂C(CH₃)(CH₂OCH₂CF₃)CH₂)$_{aa}$OH) (Fox-Diol, having a MW about 1342 and available from Omnova Solutions Inc. of Akron, Ohio).

For each of the formulas (i.e. Formulas 1-6) described herein, when X is O, Q is typically not methylene and thus contains two or more carbon atoms. In some embodiments, X is S or NR. In some embodiments, Q is an alkylene having at least two carbon atoms. In other embodiments, Q is a straight chain, branched chain, or cycle-containing connecting group selected from arylene, aralkylene, and alkarylene. In yet other embodiments, Q is a straight chain, branched chain, or cycle-containing connecting group containing a heteroatom such as O, N, and S and/or a heteroatom containing functional groups such as carbonyl and sulfonyl. In other embodiments, Q is a branched or cycle-containing alkylene group that optionally contains heteroatoms selected from O, N, S and/or a heteroatom-containing functional group such as carbonyl and sulfonyl. In some embodiments Q contains a nitrogen containing group such as amide.

The fluorocarbon- and urethane-(meth)acryl additive(s) described herein can be employed as the sole perfluoropolyether containing additive in a hardcoat composition. Alternatively, however, the additive(s) described herein may be employed in combination with various other fluorinated compounds having at least one moiety selected from fluoropolyether, fluoroalkyl, and fluoroalkylene linked to at least one free-radically reactive group with a non-urethane linking group. In these embodiments, the fluorocarbon- and urethane-(meth)acryl compositions(s) can be added to the curable mixture such that the weight ratio of the fluorocarbon urethane additive to non-urethane fluorinated material(s) is 1:1, preferably 2:1 and most preferably 3:1. Within these preferred ratios it is possible to have the total weight percent fluorine (F) of the curable mixture comprise from 0.5-25 wt % F, preferably 0.5 to 10 wt % F and most preferably 0.5 to 5 wt % F.

The perfluoropolyether moiety of the urethane is preferably a HFPO moiety, as previously described. Further, the fluorinated moiety of the second (non-urethane) compound is also preferably a HFPO moiety.

In some embodiments, the non-urethane linking group is a divalent group selected from an alkylene, arylene, or combinations thereof and optionally containing a divalent group selected from carbonyl, ester, amide, thioester or sulfonamido, and combinations thereof. In other embodiments, the linking group is a sulfur-containing heteroalkylene group containing a divalent group selected from carbonyl, ester, amide, thioester or sulfonamido, and combinations thereof. In other embodiments, the linking group is an oxygen-containing heteroalkylene group containing a divalent group selected from carbonyl, ester, thioester, sulfonamido, and combinations thereof. In yet other embodiments, the linking group is a nitrogen-containing heteroalkylene group containing a divalent group selected from carbonyl, amide, thioester, or sulfonamido, and combinations thereof.

A variety of (per)fluoropolyether(meth)acryl compounds may be employed in the (e.g. hardcoat) coating compositions in combination with the fluorocarbon- and urethane-(meth) acryl compositions. Perfluoropolyether(meth)acryl compounds can be represented by the following Formula (7):

$$(R_f)—[(W)—(R_A)]_w \quad \text{(Formula 7)}$$

wherein $R_f$ is a (per)fluoropolyether group; W is a linking group; and $R_A$ is a is a free-radically reactive such as (meth) acryl, —SH, allyl, or vinyl, and is preferably a (meth)acryl group or —COCF=$CH_2$; and w is 1 or 2.

The perfluoropolyether group $R_f$ can be linear, branched, cyclic, or combinations thereof and can be saturated or unsaturated. The perfluoropolyether has at least two catenated oxygen heteroatoms. Exemplary perfluoropolyethers include, but are not limited to, those that have perfluorinated repeating units selected from the group of —$(C_pF_{2p})$—, —$(C_pF_{2p}O)$—, —$(CF(Z))$—, —$(CF(Z)O)$—, —$(CF(Z) C_pF_{2p}O)$—, —$(C_pF_{2p}CF(Z)O)$—, —$(CF_2CF(Z)O)$—, or combinations thereof. In these repeating units, p is typically an integer of 1 to 10. In some embodiments, p is an integer of 1 to 8, 1 to 6, 1 to 4, or 1 to 3. The group Z is a perfluoroalkyl group, perfluoroether group, perfluoropolyether, or a perfluoroalkoxy group, all of which can be linear, branched, or cyclic. The Z group typically has no more than 12 carbon atoms, no more than 10 carbon atoms, or no more than 9 carbon atoms, no more than 4 carbon atoms, no more than 3 carbon atoms, no more than 2 carbon atoms, or no more than 1 carbon atom. In some embodiments, the Z group can have no more than 4, no more than 3, no more than 2, no more than 1, or no oxygen atoms. In these perfluoropolyether structures, the different repeat units can be distributed randomly along the chain.

$R_f$ can be monovalent or divalent. In some compounds where $R_f$ is monovalent, the terminal groups can be $(C_pF_{2p+1})$—, $(C_pF_{2p+1}O)$—, $(X'C_pF_{2p}O)$—, or $(X'C_pF_{2p+1})$— where X' is hydrogen, chlorine, or bromine and p is an integer of 1 to 10. In some embodiments of monovalent $R_f$ groups, the terminal group is perfluorinated and p is an integer of 1 to 10, 1 to 8, 1 to 6, 1 to 4, or 1 to 3. Exemplary monovalent $R_f$ groups include $CF_3O(C_2F_4O)_nCF_2$—, $C_3F_7O(CF_2CF_2CF_2O)_n CF_2CF_2$—, and $C_3F_7O(CF(CF_3)CF_2O)_nCF(CF_3)$— wherein n has an average value of 0 to 50, 1 to 50, 3 to 30, 3 to 15, or 3 to 10.

Suitable structures for divalent $R_f$ groups include, but are not limited to, —$CF_2O(CF_2O)_q(C_2F_4O)_nCF_2$—, —$(CF_2)_3O (C_4F_8O)_n(CF_2)_3$—, —$CF_2O(C_2F_4O)_nCF_2$—, —$CF_2\ CF_2O (CF_2CF_2CF_2O)_nCF_2CF_2$—, and —$CF(CF_3)(OCF_2CF (CF_3))_sOC_tF_{2t}O(CF(CF_3)CF_2O)_nCF(CF_3)$—, wherein q has an average value of 0 to 50, 1 to 50, 3 to 30, 3 to 15, or 3 to 10; n has an average value of 0 to 50, 3 to 30, 3 to 15, or 3 to 10; s has an average value of 0 to 50, 1 to 50, 3 to 30, 3 to 15, or 3 to 10; the sum (n+s) has an average value of 0 to 50 or 4 to 40; the sum (q+n) is greater than 0; and t is an integer of 2 to 6.

As synthesized, compounds according to Formula (7) typically include a mixture of $R_f$ groups. The average structure is the structure averaged over the mixture components. The values of q, n, and s in these average structures can vary, as long as the compound has a number average molecular weight of at least about 400. Compounds of Formula (7) often have a molecular weight (number average) of 400 to 5000, 800 to 4000, or 1000 to 3000.

The linking group W between the perfluoropolyether segment and (meth)acryl or —COCF=$CH_2$ endgroup includes a divalent group selected from an alkylene, arylene, heteroalkylene, or combinations thereof and an optional divalent group selected from carbonyl, ester, amide, sulfonamido, or combinations thereof. W can be unsubstituted or substituted with an alkyl, aryl, halo, or combinations thereof. The W group typically has no more than 30 carbon atoms. In some compounds, the W group has no more than 20 carbon atoms, no more than 10 carbon atoms, no more than 6 carbon atoms, or no more than 4 carbon atoms. For example, W can be an alkylene, an alkylene substituted with an aryl group, or an alkylene in combination with an arylene or an alkyl ether or alkyl thioether linking group.

The perfluoropolyether acrylate compounds (e.g. of Formula 7) can be synthesized by known techniques such as described in U.S. Pat. Nos. 3,553,179 and 3,544,537 as well as U.S. Pat. No. 7,094,829, "Fluorochemical Composition Comprising a Fluorinated polymer and Treatment of a Fibrous Substrate Therewith".

Suitable (non-urethane) perfluoropolyether fluorocarbon (meth)acryl compounds include for example HFPO—C(O) NH$CH_2CH_2$OC(O)CH=$CH_2$, HFPO—C(O) NH$CH_2CH_2$OC$H_2CH_2$OC$H_2CH_2$OC(O)CH=$CH_2$ HFPO—C(O)NH—$(CH_2)_6$OC(O)CH=$CH_2$ and various other (per)fluoropolyether acryl compounds such as described in U.S. Pat. No. 7,342,080 and US Publication No. 2005/0249940; incorporated by reference.

The (non-urethane) fluoropolyether poly(meth)acryl compound may also have the formula $(HFPO—)_nQ_3(X)_m$ wherein n is 1 to 3;

$Q_3$ is a straight chain, branched chain or cycle-containing connecting group having a valency of at least 2 and is selected from the group consisting of a covalent bond, an alkylene, an arylene, an aralkylene, an alkarylene; optionally containing heteroatoms O, N, and S, a heteroatom-containing functional group such as carbonyl or sulfonyl, and combinations thereof; and X is a free-radically reactive group such as (meth)acryl, —SH, allyl, or vinyl, and is preferably a (meth)acryl functional group —AC(O)C(R)=CH$_2$, where A is O, S or NR$_1$, R is a lower alkyl of 1 to 4 carbon atoms or H or F, R$_1$ is H or lower alkyl of 1 to 4 carbon atoms, and m is 2-10.

One compound is B—O(CH$_2$CH(OB)CH$_2$O)nCH$_2$CH(OB)CH$_2$O—B wherein n ranges from 0 to 20, B is independently H, —C(O)CH=CH$_2$, or —C(O)—HFPO, and in which at least one B is —C(O)—HFPO and at least two B are —C(O)CH=CH$_2$.

The (non-urethane) fluoropolyether poly(meth)acryl compound may be the reaction product of A)

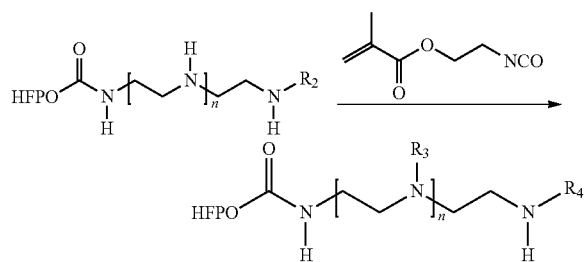

or B)

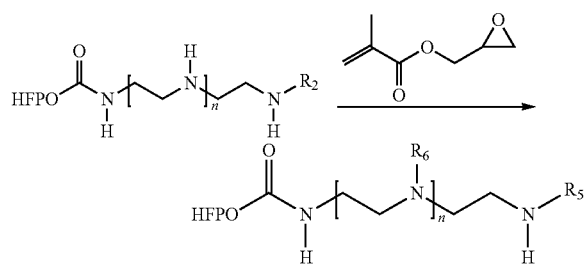

wherein
R$_2$ is hydrogen, alkyl, aryl, arylalkyl, alkylaryl, fluoroalkyl, acryl, HFPO—C(O)—,
R$_3$ is independently H or CH$_2$=C(CH$_3$)C(O)—OC$_2$H$_4$NHC(O)—,
R$_4$ is alkyl, aryl, arylalkyl, alkylaryl, fluoroalkyl, acryl, HFPO—C(O)—, or CH$_2$=C(CH$_3$)C(O)—OC$_2$H$_4$NHC(O)—,
R$_5$ is alkyl, aryl, arylalkyl, alkylaryl, fluoroalkyl, acryl, HFPO—C(O)—, or CH$_2$=C(CH$_3$)C(O)—OCH$_2$CH(OH)CH$_2$—,
R$_6$ is independently H or CH$_2$=C(CH$_3$)C(O)—OCH$_2$CH(OH)CH$_2$—, and n ranges from an average about 2 to 3.

The (e.g. non-urethane) fluoropolyether poly(meth)acryl compound may include any one or combination of the following compounds

HFPO—C(O)NHC(CH$_2$OC(O)CH=CH$_2$)$_3$;

HFPO—C(O)N(CH$_2$CH$_2$OC(O)CH=CH$_2$)$_2$;

HFPO—C(O)NHCH$_2$CH$_2$N(C(O)CH=CH$_2$)CH$_2$OC(O)CH=CH$_2$;

HFPO—C(O)NHC(CH$_2$OC(O)CH=CH$_2$)$_2$H;

HFPO—C(O)NHC(CH$_2$OC(O)CH=CH$_2$)$_2$CH$_3$;

HFPO—C(O)NHC(CH$_2$OC(O)CH=CH$_2$)$_2$CH$_2$CH$_3$;

HFPO—C(O)NHCH$_2$CH(OC(O)CH=CH$_2$)CH$_2$OC(O)CH=CH$_2$;

HFPO—C(O)NHCH$_2$CH$_2$CH$_2$N(CH$_2$CH$_2$OC(O)CH=CH$_2$)$_2$;

HFPO—C(O)OCH$_2$C(CH$_2$OC(O)CH=CH$_2$)$_3$;

HFPO—C(O)NH(CH$_2$CH$_2$N(C(O)CH=CH$_2$))$_4$CH$_2$CH$_2$NC(O)—HFPO;

CH$_2$=CHC(O)OCH$_2$CH(OC(O)HFPO)CH$_2$OCH$_2$CH(OH)CH$_2$OCH$_2$CH(OC(O)HFPO)CH$_2$OCOCH=CH$_2$;

and

HFPO—CH$_2$O—CH$_2$CH(OC(O)CH=CH$_2$)CH$_2$OC(O)CH=CH$_2$

In other embodiments, the non-urethane fluoropolyether poly(meth)acryl compound may be a compound preparable by Michael-type addition of a reactive (per)fluoropolyether with a poly(meth)acrylate, such as the adduct of HFPO—C(O)N(H)CH$_2$CH$_2$CH$_2$N(H)CH$_3$ with trimethylolpropane triacrylate (TMPTA). Such (per)fluoropolyether acrylate compounds are further described in U.S. Pat. No. 7,342,080.

Other non-urethane fluoropolyether poly(meth)acryl compounds include those disclosed in U.S. Pat. Nos. 3,810,874 and 4,321,404. A representative compound is given by the structure CH$_2$=CHC(O)OCH$_2$CF$_2$O(CF$_2$CF$_2$O)$_{mm}$(CF$_2$O)$_{nn}$CH$_2$OC(O)CH=CH$_2$,
where mm and nn designate that the number of randomly distributed perfluoroethyleneoxy and perfluoromethyleneoxy backbone repeating units, respectively, mm and nn having independently values, for example from 1 to 50, and the ratio of mm/nn is 0.2 to 1 to 5/1.

Still other non-urethane fluoropolyether compounds include thiols such as HFPO—C(O)NHCH$_2$CH$_2$OC(O)CH$_2$SH and vinyl compounds such as HFPO—C(O)NHCH$_2$CH=CH$_2$, and HFPO—C(O)NHCH$_2$CH$_2$OCH=CH$_2$.

In one synergistic combination, a perfluoropolyether urethane having a perfluoropolyether moiety and a multi-(meth)acryl terminal group is employed in combination with a (non-urethane) monofunctional perfluoropolyether compound having a perfluoropolyether moiety linked to a (meth)acryl group. Typically, the perfluoropolyether moiety is a terminal group of the compound. Likewise, the (meth)acryl group is also typically a terminal group. In another embodiment, the second (non-urethane) perfluoropolyether compound typically has a higher weight percent fluorine than the perfluoropolyether urethane multi-(meth)acryl compound. It is surmised that the monofunctional perfluoropolyether compound is the major contributor to the high contact angles; whereas the perfluoropolyether urethane multi-(meth)acryl compound compatibilizes the monofunctional perfluoropolyether compound. This interaction allows higher concentration of monofunctional perfluoropolyether compound to be incorporated without phase separation. In yet another embodiment, a perfluoropolyether urethane having a perfluoropolyether moiety and a multi-(meth)acryl terminal group is employed in combination with a (non-urethane) multi-functional perfluoropolyether compound having a perfluoropolyether moiety linked to at least two (meth)acryl group. Alternatively, a perfluoropolyether urethane monoacrylate can be employed in combination with a (non-urethane) mono- or multi-(meth)acryl perfluoropolyether compound.

The fluorocarbon- and urethane(meth)acryl additives (e.g. such as those of Formulas (1), (3A), (4), (5) or (6)), optionally in combination with various other (per)fluoropolyether (meth)acryl compounds, may also be combined with one or more other (non-urethane) fluorinated compounds to improve the compatibility of the mixture.

A class of free-radically reactive fluoroalkyl or fluoroalkylene group-containing compatibilizers includes compounds of the respective chemical formulas: $R_f Q_3 (X_1)_{n1}$ and $(X_1)_{n1} Q_3 R_{f2} Q_3 (X_1)_{n1}$, where $R_f$ is a fluoroalkyl, $R_{f2}$ is a fluoroalkylene, $Q_3$ is a connecting group of valency at least 2 and is selected from the group consisting of a covalent bond, an alkylene, an arylene, an aralkylene, an alkarylene group, a straight or branched chain or cycle-containing connecting group optionally containing heteroatoms such as O, N, and S and optionally a heteroatom-containing functional group such as carbonyl or sulfonyl, and combinations thereof; $X_1$ is a free-radically reactive group selected from (meth)acryl, —SH, allyl, or vinyl groups and n1 is independently 1 to 3. Typical $Q_3$ groups include: —$SO_2N(R)CH_2CH_2$—; —$SO_2N(CH_2CH_2)_2$—; —$(CH_2)_m$—; —$CH_2O(CH_2)_3$—; and —$C(O)NRCH_2CH_2$—, where R is H or lower alkyl of 1 to 4 carbon atoms and m is 1 to 6. Preferably the fluoroalkyl or fluoroalkylene group is a perfluoroalkyl or perfluoroalkylene group. One preferred class of fluoroalkyl- or alkylene-substituted compatibilizers meeting these criteria for use in the composition of the hard coat layer 18 is the perfluorobutyl-substituted acrylate compatibilizers. Exemplary, non-limiting perfluorobutyl-substituted acrylate compatibilizers meeting these criteria and useful in the present invention include one or more of $C_4F_9SO_2N(CH_3)CH_2CH_2OC(O)CH=CH_2$, $C_4F_9SO_2N(CH_2CH_2OC(O)CH=CH_2)_2$, or $C_4F_9SO_2N(CH_3)CH_2CH_2OC(O)C(CH_3)=CH_2$. The free-radically reactive fluoroalkyl or fluoroalkylene group-containing compatibilizers described above are preferably added at between about 0.5% and 20%, and more preferably between about 1% and 10%, of the total solids of the hard coat composition.

One non-limiting example of a preferred fluoroalkyl-substituted compatibilizer that may be utilized in the composition of the hard coat layer 18 is: (1H,1H,2H,2H)-perfluorodecyl acrylate, available from Lancaster Synthesis of Windham, N.H. Numerous other (meth)acryl compounds with perfluoroalkyl moieties that may also be utilized in the composition of the hard coat layer are mentioned in U.S. Pat. No. 4,968,116, to Hulme-Lowe et al., and in U.S. Pat. No. 5,239,026 (including perfluorocyclohexylmethyl methacrylate), to Babirad et al., which are herein incorporated by reference. Other fluorochemical (meth)acrylates that meet these criteria and may be utilized include, for example, 2,2,3,3,4,4,5,5-octafluorohexanediol diacrylate and ω-hydro 2,2,3,3,4,4,5,5-octafluoropentyl acrylate ($H—C_4F_8—CH_2O—C(O)—CH=CH_2$). Other fluorochemical (meth)acrylates that may be used alone, or as mixtures, are described in U.S. Pat. No. 6,238,798, to Kang et al., and herein incorporated by reference.

Another compatibilizer that may be used is a fluoroalkyl- or fluoroalkylene-substituted thiol or polythiol. Non-limiting examples of this type of compatibilizer includes one or more of the following: $C_4F_9SO_2N(CH_3)CH_2CH_2OC(O)CH_2SH$, $C_4F_9SO_2N(CH_3)CH_2CH_2OC(O)CH_2CH_2SH$, $C_4F_9SO_2N(CH_3)CH_2CH_2SH$, and $C_4F_9SO_2N(CH_3)CH(OC(O)CH_2SH)CH_2OC(O)CH_2SH$.

In some embodiments, as little as 1 wt-% of the non-urethane fluorinated compound will phase separate from a hydrocarbon multifunctional acrylate such as trimethyol propane triacrylate. Such phase separation is undesirable in the hardcoats of this invention since it can lead to optically non-uniform coatings. In these embodiments, the fluorocarbon- and urethane-(meth)acryl compositions(s) can be added to the curable mixture such that the weight ratio of the fluorocarbon urethane additive to non-urethane perfluoropolyether, fluoroalkyl, or fluoroalkylene (meth)acryl compound is 1:1, preferably 2:1 and most preferably 3:1. Within these preferred ratios the total weight percent fluorine of the curable mixture may comprise from 0.5-25 wt-% fluorine, preferably 0.5 to 10 wt-% fluorine, and most preferably 0.5 to 5-wt % fluorine, without the non-urethane fluorinated (meth)acryl compound phase separating from the mixture. The non-urethane containing perfluoropolyether can have molecular weights of greater than 300 g/mol to 3000 g/mol, contain mono(meth)acryl functionality, or multi-(meth)acryl functionality. The (meth)acryl functionality can be located at one or both termini or as a branch point in the molecule.

The hardcoat may be provided as a single layer disposed on an optical substrate. In this construction, the total of all (per)fluorinated compounds, (e.g. the perfluoropolyether urethane(s) alone or in combination with other fluorinated compounds) ranges from 0.01% to 10%, and more preferably from 0.1% to 1%, of the total solids of the hard coat composition. For embodiments wherein a (e.g. inorganic particle-containing) hardcoat layer is disposed between the optical substrate and hardcoat surface layer, the amount of perfluoropolyether urethane(s) in the coating compositions ranges from 0.01 to 50 wt-% solids, and more preferably from 1 to 25 wt-% solids; whereas the various other (per)fluoropolyether acryl compounds may be present at weight percents from 1 to 20%, and preferably from 1 to 10%. Preferably, the ratio of fluorocarbon- and urethane-(meth)acryl-containing additive to other non-urethane fluorinated compounds is at least 1 to 1 and more preferably is about 3 to 1.

The conventional hard coat material used as a portion of layer 18 in any of the preferred embodiments described above is a hydrocarbon-based material well known to those of ordinary skill in the optical arts. Most preferably, the hydrocarbon-based material is an acrylate-based hard coat material. One preferable hard coat material for use in the present invention is based on PETA (pentaerythritol tri/tetra acrylate). One commercially available form of pentaerythritol triacrylate ("PET3A") is SR444C and one commercially available form of pentaerythritol tetraacrylate ("PET4A") is SR295, each available from Sartomer Company of Exton, Pa.

However, other crosslinking agents may be used in the present invention. Useful crosslinking agents include, for example, poly(meth)acryl monomers selected from the group consisting of (a) di(meth)acryl containing compounds such as 1,3-butylene glycol diacrylate, 1,4-butanediol diacrylate, 1,6-hexanediol diacrylate, 1,6-hexanediol monoacrylate monomethacrylate, ethylene glycol diacrylate, alkoxylated aliphatic diacrylate, alkoxylated cyclohexane dimethanol diacrylate, alkoxylated hexanediol diacrylate, alkoxylated neopentyl glycol diacrylate, caprolactone modified neopentylglycol hydroxypivalate diacrylate, caprolactone modified neopentylglycol hydroxypivalate diacrylate, cyclohexanedimethanol diacrylate, diethylene glycol diacrylate, dipropylene glycol diacrylate, ethoxylated (10) bisphenol A diacrylate, ethoxylated (3) bisphenol A diacrylate, ethoxylated (30) bisphenol A diacrylate, ethoxylated (4) bisphenol A diacrylate, hydroxypivaldehyde modified trimethylolpropane diacrylate, neopentyl glycol diacrylate, polyethylene glycol (200) diacrylate, polyethylene glycol (400) diacrylate, polyethylene glycol (600) diacrylate, propoxylated neopentyl glycol diacrylate, tetraethylene glycol diacrylate, tricyclodecanedimethanol diacrylate, triethylene glycol diacrylate, tripropylene glycol diacrylate; (b) tri(meth)acryl containing compounds such as glycerol triacrylate, trimethylolpropane triacrylate, ethoxylated triacrylates (e.g., ethoxylated (3) trimethylolpropane triacrylate, ethoxylated (6) trimethylolpropane triacrylate, ethoxylated (9) trimethylolpropane triacrylate, ethoxylated (20) trimethylolpropane triacrylate), propoxylated triacrylates (e.g., propoxylated (3) glyceryl triacrylate, propoxylated (5.5) glyceryl triacrylate, propoxylated (3) trimethylolpropane triacrylate, propoxylated (6) trimethylolpropane triacrylate), trimethylolpropane triacrylate, tris(2-hydroxyethyl)isocyanurate triacrylate; (c) higher functionality (meth)acryl containing compounds such as ditrimethylolpropane tetraacrylate, dipentaerythritol pentaacrylate, ethoxylated (4) pentaerythritol tetraacrylate, caprolactone modified dipentaerythritol hexaacrylate; (d) oligomeric (meth)acryl compounds such as, for example, urethane acrylates, polyester acrylates, epoxy acrylates; polyacrylamide analogues of the foregoing; and combinations thereof. Such compounds are widely available from vendors such as, for example, Sartomer Company of Exton, Pa.; UCB Chemicals Corporation of Smyrna, Ga.; and Aldrich Chemical Company of Milwaukee, Wis. Additional useful (meth)acrylate materials include hydantoin moiety-containing poly(meth)acrylates, for example, as described in U.S. Pat. No. 4,262,072 (Wendling et al.).

It is typically preferred to maximize the concentration of crosslinker particularly since non-fluorinated (meth)acrylate crosslinkers are generally less expensive than fluorinated compounds. Accordingly, the coating compositions described herein typically comprise at least 20 wt-% crosslinking agent(s). The total amount of crosslinking agent(s) may comprise at least 50 wt-% and may be for example at least 60 wt-%, at least 70 wt-%, at least 80 wt-%, at least 90 wt-% and even about 95 wt-% of the coating composition.

To facilitate curing, polymerizable compositions according to the present invention may further comprise at least one free-radical thermal initiator and/or photoinitiator. Typically, if such an initiator and/or photoinitiator are present, it comprises less than about 10 percent by weight, more typically less than about 5 percent of the polymerizable composition, based on the total weight of the polymerizable composition. Free-radical curing techniques are well known in the art and include, for example, thermal curing methods as well as radiation curing methods such as electron beam or ultraviolet radiation. Further details concerning free radical thermal and photopolymerization techniques may be found in, for example, U.S. Pat. No. 4,654,233 (Grant et al.); U.S. Pat. No. 4,855,184 (Klun et al.); and U.S. Pat. No. 6,224,949 (Wright et al.).

Useful free-radical thermal initiators include, for example, azo, peroxide, persulfate, and redox initiators, and combinations thereof.

Useful free-radical photoinitiators include, for example, those known as useful in the UV cure of acrylate polymers. Such initiators include benzophenone and its derivatives; benzoin, alpha-methylbenzoin, alpha-phenylbenzoin, alpha-allylbenzoin, alpha-benzylbenzoin; benzoin ethers such as benzil dimethyl ketal (commercially available under the trade designation "IRGACURE 651" from Ciba Specialty Chemicals Corporation of Tarrytown, N.Y.), benzoin methyl ether, benzoin ethyl ether, benzoin n-butyl ether; acetophenone and its derivatives such as 2-hydroxy-2-methyl-1-phenyl-1-propanone (commercially available under the trade designation "DAROCUR 1173" from Ciba Specialty Chemicals Corporation) and 1-hydroxycyclohexyl phenyl ketone (commercially available under the trade designation "IRGACURE 184", also from Ciba Specialty Chemicals Corporation); 2-methyl-1-[4-(methylthio)phenyl]-2-(4-morpholinyl)-1-propanone commercially available under the trade designation "IRGACURE 907", also from Ciba Specialty Chemicals Corporation); 2-benzyl-2-(dimethylamino)-1-[4-(4-morpholinyl)phenyl]-1-butanone commercially available under the trade designation "IRGACURE 369" from Ciba Specialty Chemicals Corporation); aromatic ketones such as benzophenone and its derivatives and anthraquinone and its derivatives; onium salts such as diazonium salts, iodonium salts, sulfonium salts; titanium complexes such as, for example, that which is commercially available under the trade designation "CGI 784 DC", also from Ciba Specialty Chemicals Corporation); halomethylnitrobenzenes; and mono- and bis-acylphosphines such as those available from Ciba Specialty Chemicals Corporation under the trade designations "IRGACURE 1700", "IRGACURE 1800", "IRGACURE 1850", "IRGACURE 819" "IRGACURE 2005", "IRGACURE 2010", "IRGACURE 2020" and "DAROCUR 4265". Combinations of two or more photoinitiators may be used. Further, sensitizers such as 2-isopropyl thioxanthone, commercially available from First Chemical Corporation, Pascagoula, Miss., may be used in conjunction with photoinitiator(s) such as ""IRGACURE 369".

The composition of any of these embodiments is applied to an optical substrate layer or light transmissible substrate and photocured to form the easy to clean, stain and ink repellent light transmissible surface layer. The presence of the urethane functionality, in addition to the fluorocarbon component, in the additive can eliminate the need for comonomers introduced to the composition to compatibilize the fluorochemical component with the hydrocarbon-based crosslinker.

The polymerizable coating composition for use as the surface layer or underlying hardcoat layer preferably contains surface modified inorganic particles that add mechanical strength to the resultant coating.

A variety of inorganic oxide particles can be used in the hardcoat. The particles are typically substantially spherical in shape and relatively uniform in size. The particles can have a substantially monodisperse size distribution or a polymodal distribution obtained by blending two or more substantially monodisperse distributions. The inorganic oxide particles are typically non-aggregated (substantially discrete), as aggregation can result in precipitation of the inorganic oxide particles or gelation of the hardcoat. The inorganic oxide particles are typically colloidal in size, having an average particle diameter of about 0.001 to about 0.2 micrometers, less than about 0.05 micrometers, and less than about 0.03 micrometers. These size ranges facilitate dispersion of the inorganic oxide particles into the binder resin and provide ceramers with desirable surface properties and optical clarity. The average particle size of the inorganic oxide particles can be measured using transmission electron microscopy to count the number of inorganic oxide particles of a given diameter. The inorganic oxide particles can consist essentially of or consist of a single oxide such as silica, or can comprise a combination of oxides, such as silica and aluminum oxide, or a core of an oxide of one type (or a core of a material other than a metal oxide) on which is deposited an oxide of another type. Silica is a common inorganic particle. The inorganic oxide particles are often provided in the form of a sol containing a colloidal dispersion of inorganic oxide particles in liquid media. The sol can be prepared using a variety of techniques and in a variety of forms including hydrosols (where water serves as the liquid medium), organosols (where organic liquids so serve), and mixed sols (where the liquid medium contains both water and an organic liquid), e.g., as described in U.S. Pat. No. 5,648,407 (Goetz et al.); U.S. Pat. No. 5,677,050 (Bilkadi et al.) and U.S. Pat. No. 6,299,799 (Craig et al.), the disclosure of which is incorporated by reference herein. Aqueous sols (e.g. of amorphous silica) can be employed. Sols generally contain at least 2 wt-%, at least 10 wt-%, at least 15 wt-%, at least 25 wt-%, and often at least 35 wt-% colloidal inorganic oxide particles based on the total weight of the sol. The amount of colloidal inorganic oxide particle is typically no more than 50 wt-% (e.g. 45 wt-%). The surface of the inorganic particles can be "acrylate functionalized" as described in Bilkadi et al. The sols can also be matched to the pH of the binder, and can contain counterions or water-soluble compounds (e.g., sodium aluminate), all as described in Kang et al. '798.

One example of such particles is colloidal silica reacted with a methacryl silane coupling agent such as A-174 (available from Natrochem, Inc.), other dispersant aids such as N,N dimethylacrylamide and various other additives (stabilizers, initiators, etc.).

A particulate matting agent can be incorporated into the polymerizable composition in order to impart anti-glare properties to the surface layer. The particulate matting agent also prevents the reflectance decrease and uneven coloration caused by interference with an associated hard coat layer. The particulate matting agent should preferably be transparent, exhibiting transmission values of greater than about 90%. Alternatively, or in addition thereto, the haze value is preferably less than about 5%, and more preferably less than about 2%, and most preferably less than about 1%.

Exemplary systems incorporating matting agents into a hard coating layer, but having a different hard coating composition, are described, for example, in U.S. Pat. No. 6,693,746, and herein incorporated by reference. Further, exemplary matte films are commercially available from U.S.A. Kimoto Tech of Cedartown, Ga., under the trade designation "N4D2A."

The amount of particulate matting agent added is between about 0.5 and 10% of the total solids of the composition, depending upon the thickness of the layer 18, with a preferred amount around 2%. The anti-glare layer 18 preferably has a thickness of 0.5 to 10 microns, more preferably 0.8 to 7 microns, which is generally in the same thickness range of gloss hard coatings.

The average particle diameter of the particulate matting agent has a predefined minimum and maximum that is partially dependent upon the thickness of the layer. However, generally speaking, average particle diameters below 1.0 microns do not provide the degree of anti-glare sufficient to warrant inclusion, while average particle diameters exceeding 10.0 microns deteriorate the sharpness of the transmission image. The average particle size is thus preferably between about 1.0 and 10.0 microns, and more preferably between 1.7 and 3.5 microns, in terms of the number-averaged value measured by the Coulter method.

As the particulate matting agent, inorganic particles or resin particles are used including, for example, amorphous silica particles, $TiO_2$ particles, $Al_2O_3$ particles, cross-linked acrylic polymer particles such as those made of cross-linked poly(methyl methacrylate), cross-linked polystyrene particles, melamine resin particles, benzoguanamine resin particles, and cross-linked polysiloxane particles. By taking into account the dispersion stability and sedimentation stability of the particles in the coating mixture for the anti-glare layer and/or the hard coat layer during the manufacturing process, resin particles are more preferred, and in particular cross-linked polystyrene particles are preferably used since resin particles have a high affinity for the binder material and a small specific gravity.

As for the shape of the particulate matting agent, spherical and amorphous particles can be used. However, to obtain a consistent anti-glare property, spherical particles are desirable. Two or more kinds of particulate materials may also be used in combination.

Other types of inorganic particles can be incorporated into the hard coats of this invention. Particularly preferred are conducting metal oxide nanoparticles such as antimony tin oxide, fluorinated tin oxide, vanadium oxide, zinc oxide, antimony zinc oxide, and indium tin oxide. They can also be surface treated with materials such as 3-methacryloxypropyltrimethoxysilane. These particles can provide constructions with antistatic properties. This is desirable to prevent static charging and resulting contamination by adhesion of dust and other unwanted debris during handling and cleaning of the film. Preferably, such metal oxide particles are incorporated into the top (thin) layer of the two-layer constructions of this invention, in which the fluorinated hardcoat is applied to a hydrocarbon-based hardcoat. At the levels at which such particles may be needed in the coating in order to confer adequate antistatic properties (typically 25 wt % and greater), these deeply colored particles can impart undesired color to the construction. However, in the thin top layer of a two-layer fluorinated hardcoat construction, their effect on the optical and transmission properties of the film is minimized Examples of conducting metal oxide nanoparticles useful in this embodiment include antimony double oxide available from Nissan Chemical under the trade designations Celnax CXZ-210IP and CXZ-210IP-F2. When these particles are included at appropriate levels in the coatings of this invention, the resulting fluorinated hardcoats can exhibit static charge decay times less than about 0.5 sec. In this test, the sample is placed between two electrical contacts and charged to +/−5 kV. The sample is then grounded, and the time necessary for the charge to decay to 10% of its initial value is measured and recorded as the static charge decay time. In contrast, film constructions containing no conducting nanoparticles exhibit static charge decay times>30 sec.

Thin coating layers 18 of any of the preferred embodiments can be applied to the optical substrate 16 using a variety of techniques, including dip coating, forward and reverse roll coating, wire wound rod coating, and die coating. Die coaters include knife coaters, slot coaters, slide coaters, fluid bearing coaters, slide curtain coaters, drop die curtain coaters, and extrusion coaters among others. Many types of die coaters are described in the literature such as by Edward Cohen and Edgar Gutoff, Modern Coating and Drying Technology, VCH Publishers, N.Y. 1992, ISBN 3-527-28246-7 and Gutoff and Cohen, Coating and Drying Defects: Troubleshooting Operating Problems, Wiley Interscience, N.Y. ISBN 0-471-59810-0.

A die coater generally refers to an apparatus that utilizes a first die block and a second die block to form a manifold cavity and a die slot. The coating fluid, under pressure, flows through the manifold cavity and out the coating slot to form a ribbon of coating material. Coatings can be applied as a single layer or as two or more superimposed layers. Although it is usually convenient for the substrate to be in the form of a continuous web, the substrate may also be a succession of discrete sheets.

To prove the effectiveness of the hard coat formulations according to each preferred embodiment of the present invention described above, sample hard coats having the given compositions were formulated and applied to PET substrates and compared to hard coat formulations having less than all the desired components. The coatings were visually inspected and tested for ink repellency, durability and surface roughness. The experimental procedures and tabulated results are described below:

I. EXPERIMENTAL PROCEDURES

A: Ingredients

Unless otherwise noted, as used in the examples, "HFPO—" refers to the end group $F(CF(CF_3)CF_2O)_aCF(CF_3)$— of the methyl ester $F(CF(CF_3)CF_2O)_aCF(CF_3)C(O)OCH_3$ wherein a averages about 6.22, with an average molecular weight of 1,211 g/mol, can be prepared according to the method reported in U.S. Pat. No. 3,250,808 (Moore et al.), the disclosure of which is incorporated herein by reference, with purification by fractional distillation.

Polyisocyanates Desmodur™ (Des) N100, Desmodur™ 3300, Desmodur™ TPLS2294, Desmodur™ N 3600, and Isophorone diisocyanate (IPDI) were obtained from Bayer Polymers LLC, of Pittsburgh, Pa.

PAPI (Poly[(phenyl isocyanate)-co-formaldehyde]) (MW about 375), is available from Sigma Aldrich of Milwaukee, Wis.

$C_6F_{13}C_2H_4OH$ is available from Sigma Aldrich of Milwaukee, Wis.

4-methoxy phenol (MEHQ) is available from Sigma Aldrich of Milwaukee, Wis. $HO(CH_2)_{10}OH$ is available from Sigma Aldrich of Milwaukee, Wis.

FOX-diol $(H(OCH_2CCH_3(CH_2OCH_2CF_3)CH_2)_xOH)$ (MW about 1342), is available from Omnova Solutions Inc. of Akron, Ohio.

Pentaerythritol tetraacrylate ("PET4A"), under the trade designation "SR295", was obtained from Sartomer Company of Exton, Pa.

Pentaerythritol triacrylate ("PET3A"), under the trade designation "SR444C", was obtained from Sartomer Company of Exton, Pa.

Trimethylolpropane triacrylate ("TMPTA"), under the trade designation "SR351", was obtained from Sartomer Company of Exton, Pa.

Hydantoin hexaacrylate (HHA) was prepared as described in Example 1 of U.S. Pat. No. 4,262,072.

FBSEE $(C_4F_9SO_2N(C_2H_4OH)_2)$, a fluorochemical diol, can be prepared as described in column 5, line 31 and in FIG. 9 of U.S. Pat. No. 3,734,962 (1973).

MeFBSE $(C_4F_9SO_2N(CH_3)CH_2CH_2OH)$ was prepared by essentially following the procedure described in U.S. Pat. No. 6,664,354 (Savu et al.), Example 2, Part A.

FBSEA $(C_4F_9SO_2N(CH_3)CH_2CH_2OC(O)CH=CH_2)$ is made by the procedure of Examples 2A and 2B of WO 01/30873 to Savu et al.

HFPO-AEA $(HFPO—C(O)NHCH_2CH_2OC(O)CH=CH_2)$ was prepared as described in File number U.S. Pat. No. 7,101,618; under Preparation of Monofunctional Perfluoropolyether Acrylate (FC-1). Hereafter its use is noted as 31a.

Fomblin Zdol $(HOCH_2CF_2(OCF_2CF_2)_n(OCF_2)_mCH_2OH)$ is available from Solvay Solexis, Inc. of Italy.

LTM diacrylate, $CH_2=CHC(O)OCH_2CF_2O(CF_2CF_2O)_{mm}(CF_2O)_{nn}CH_2OC(O)CH=CH_2$, was prepared from Fomblin Zdol according to the procedure of Example XV of U.S. Pat. No. 3,810,874.

Hydroxyethyl acrylate (HEA) is available from Sigma Aldrich of Milwaukee, Wis.

$H_2NCH_2CH_2CH_2Si(OCH_3)_3$ is available from Sigma Aldrich of Milwaukee, Wis.

$HSCH_2CH_2CH_2Si(OCH_3)_3$ is available from Sigma Aldrich of Milwaukee, Wis.

2-isocyanato-ethyl methacrylate ("IEM") $(CH_2=C(CH_3)CO_2CH_2CH_2NCO)$, is available from Sigma Aldrich of Milwaukee, Wis.

CN 4000 is available from Sartomer Company of Exton, Pa. It is an α,ω difunctional perfluoropolyether oligomer with 55% wt fluorine and a molecular weight of approximately 2000 g/mol.

The amines, triethylamine, 2-amino-2-ethyl-1,3-propanediol, and 1,1-bis-(hydroxyethyl)-1,3 aminopropane were obtained from Sigma-Aldrich of Milwaukee, Wis.

Acryloyl chloride was obtained from Sigma-Aldrich of Milwaukee Wis.

The UV photoinitiator, 1-hydroxycyclohexyl phenyl ketone used was obtained from Ciba Specialty Products, Tarrytown, N.Y. and sold under the trade designation "Irgacure 184."

The photoinitiator 2-methyl-1-[4-(methylthio)phenyl]-2-morpholinopropan-1-one used was obtained from Ciba Specialty Products, Tarrytown, N.Y. and sold under the trade designation "Irgacure 907."

Methyl perfluorobutyl ether (HFE 7100) was obtained from 3M Company, St. Paul, Minn.

Dibutyltin dilaurate (DBTDL) was obtained from Sigma Aldrich of Milwaukee, Wis.

B. Preparation of Experimental Materials

Unless otherwise noted, "MW" refers to molecular weight and "EW" refers to equivalent weight. Further, "° C." may be used interchangeably with "degrees Celsius" and "mol" refers to moles of a particular material and "eq" refers to equivalents of a particular material. Further, "Me" constitutes a methyl group and may be used interchangeably with "$CH_3$."

Preparation No. 1. Preparation of HFPO—C(O)OCH$_3$

As used in the examples, "HFPO—" refers to the end group $F(CF(CF_3)CF_2O)_aCF(CF_3)$— wherein a has average values of about 4.41, 6.2, 6.85, and 8.07. The material $F(CF(CF_3)CF_2O)_aCF(CF_3)COOCH_3$ (HFPO—C(O)OCH$_3$) can be prepared according to the method reported in U.S. Pat. No. 3,250,808 (Moore et al.), the disclosure of which is incorporated herein by reference, with purification by fractional distillation.

Preparation No. 2. Preparation of HFPO diol
HFPO—C(O)NHCH$_2$CH$_2$CH$_2$N(CH$_2$CH$_2$OH)$_2$(HFPODO, MW about 1341)

To a 500 ml 3-necked flask equipped with a stir bar and reflux condenser was charged 100 g (MW about 1210.6, 0.0826 mol) HFPO—C(O)OCH$_3$, and 13.40 g (MW=162.2, 0.0826 mol) H$_2$NCH$_2$CH$_2$CH$_2$N(CH$_2$CH$_2$OH)$_2$. The mixture was reacted neat at 130 degrees Celsius for 6 hours. From Fourier Transform Infrared Spectroscopy (FTIR) analysis, the amide —C(O)NH— was formed as the ester signal (—CO$_2$—) disappeared. The desired product, HFPO—C(O)NHCH$_2$CH$_2$CH$_2$N(CH$_2$CH$_2$OH)$_2$ was obtained as a viscous yellow liquid after concentration at 55 degrees Celsius under aspirator vacuum.

Preparation No. 3. Preparation of HFPO—C(O)N(H)C(CH$_2$OH)$_2$CH$_2$CH$_3$ Starting Material To a 500 ml 3-necked flask equipped with a stir bar and reflux condenser was charged 11.91 g (0.1 mol) H$_2$NC(CH$_2$OH)$_2$CH$_2$CH$_3$ and 60 g tetrahydrofuran ("THF"). Next via dropping funnel was added 121.1 g (0.1 mol) HFPO—C(O)OCH$_3$ over about 80 minutes at a bath temperature of about 85 degrees Celsius. The reaction was cloudy at first, but became clear about 1 hour into the reaction. After addition was complete, the heating bath was shut off and the reaction was allowed to cool for three days. The material was concentrated at 55 degrees Celsius under aspirator vacuum to yield 130.03 g of a light colored syrup. NMR analysis showed the product to be an 87:13 mixture of the structures I and II as follows:

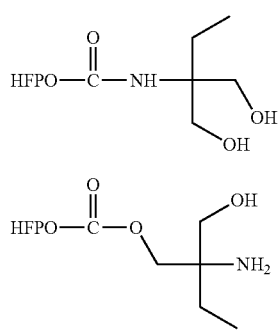

Structure I

Structure II

Preparation No. 4a. Preparation of HFPO—C(O)NHCH$_2$CH$_2$OH

HFPO—C(O)N(H)CH$_2$CH$_2$OH of different molecular weights (938.5, 1344, and 1547.2) were made by a procedure similar to that described in U.S. Pat. No. 7,094,829, with the exception that F(CF(CF$_3$)CF$_2$O)$_a$CF(CF$_3$)C(O)CH$_3$ with a=6.2 was replaced with F(CF(CF$_3$)CF$_2$O)$_a$CF(CF$_3$)C(O)OCH$_3$ wherein a=4.41, 6.85, and 8.07 respectively.

Preparation No. 4b, Synthesis of HFPOC(O)—NH—CH$_2$CH$_2$—O—CH$_2$CH$_2$—OCH$_2$CH$_2$—OH Starting Material (i.e. HFPO-EO3-OH)HFPO—C(O)OCH$_3$ (Mw=1340 g/mole. 100.0 g) was placed in a 500 ml round bottom flask. The flask was purged with nitrogen and placed in a water bath to maintain a temperature of 50° C. or less. To this flask was added 9.5 g (0.091 mol) of 2-aminoethoxyethoxyethanol (obtained from Huntsman Chemicals of Austin, Tex. as XTA-250). The reaction mixture was observed to be initially two phases, but with stirring, it gradually turned light yellow and homogenized within about 30 min. The reaction mixture was allowed to stir for 48 hrs. After this time an infrared spectrum of the reaction mixture showed complete loss of the methyl ester band at 1780 cm$^{-1}$ and the presence of the strong amide carbonyl stretch at 1718 cm$^{-1}$. Methyl t-butyl ether (200 ml) was added to the reaction mixture and the organic phase was extracted twice with water/HCl (~15%) to remove unreacted amine and methanol. The MTBE layers were combined and dried with MgSO$_4$. The MTBE was removed under reduced pressure to yield a clear, viscous liquid. Further drying at 0.1 mm Hg at room temperature for 16 hrs, resulted in 101.3 g (90% yield). $^1$H NMR and IR spectroscopy confirmed the formation of the above-identified compound HFPO-EO3-OH.

Preparation No. 4c, Synthesis of HFPOC(O)—NH—CH$_2$CH$_2$—O—CH$_2$CH$_2$—O—CH$_2$CH$_2$O—CH$_2$CH$_2$O—OH Starting Material (i.e. HFPO-EO4-OH)

The same synthetic process was used for the preparation of HFPO-EO4-OH as the EO3-OH adduct except the starting amino-EO4-alcohol, aminoethoxyethoxyethoxy ethanol was used instead of amino EO3. EO4-alcohol was obtained from Huntsman Chemicals of Austin, Tex. as XTA-350.

Preparation No. 4d, Synthesis of HFPOC(O)—NH—(CH$_2$)$_6$—OH Starting Material (i.e. HFPO-AH-OH)

The same synthetic procedure was used for the preparation of HFPO-AH-OH as the EO3-OH adduct except the starting aminoalcohol was 6-amino-hexanol available from Aldrich Chemical Co. Milwaukee, Wis.

C. General Procedure-Synthesis of Perfluoropolyether Urethane Multiacrylate

Preparation No. 5. Preparation of Des N100/0.66 PET3A/0.33 HFPO

A 500 ml roundbottom flask equipped with magnetic stir bar was charged with 25.0 g (0.131 eq, 191 EW) Des N100, 43.13 g (0.087 eq, 494.3 EW) of Sartomer SR444c, 25.3 mg of MEHQ, and 126.77 g methyl ethyl ketone (MEK). The reaction was swirled to dissolve all the reactants, the flask was placed in a oil bath at 60 degrees Celsius, and fitted with a condenser under dry air. Two drops of dibutyltin dilaurate was added to the reaction. After 1 hour, 58.64 g (0.0436 eq, 1344 EW) F(CF(CF$_3$)CF$_2$O)$_{6.85}$CF(CF$_3$)C(O)NHCH$_2$CH$_2$OH was added to the reaction via addition funnel over about 75 minutes. The reaction was monitored by FTIR and showed a small isocyanate absorption at 2273 cm$^{-1}$ after about 5 hours of reaction, but no isocyanate absorption at 7.5 hours of reaction. The material was used as a 50% solids solution in MEK. The HFPO multiacrylate urethanes preparations shown in Table 1 below, listed as Preparation Nos. 5.1 through 5.19 respectively, were all made according to this general procedure, using the appropriate mole fractions of materials noted in the table.

TABLE 1

Perfluoropolyether Urethane Multiacrylates

| Preparation Number | Isocyanate used (set at 100 Mole percent NCO in all cases) | Mole percent PET3A | Mole percent HFPO—C(O)NHCH$_2$CH$_2$OH (MW 1344) |
|---|---|---|---|
| 5.1 | Des N100 | 95 | 5 |
| 5.2 | Des N100 | 85 | 15 |
| 5.3 | Des N100 | 75 | 25 |
| 5.4 | Des N100 | 66.6 | 33.3 |
| 5.5 | Des N100 | 50 | 50 |
| 5.6 | Des N100 | 33.3 | 66.6 |
| 5.7 | Des N100 | 5 | 95 |
| 5.8 | Des N3300 | 85 | 15 |

TABLE 1-continued

Perfluoropolyether Urethane Multiacrylates

| Preparation Number | Isocyanate used (set at 100 Mole percent NCO in all cases) | Mole percent PET3A |
|---|---|---|
| 5.9 | Des N3300 | 75 | 25 |
| 5.10 | Des N3300 | 66.6 | 33.3 |
| 5.11 | Des N3300 | 50 | 50 |
| 5.12 | IPDI | 75 | 25 |
| 5.13 | Des TPLS2294 | 85 | 15 |
| 5.14 | Des N3600 | 85 | 15 |
| | | | Mole percent HFPO—C(O)NH(CH$_2$)$_3$NHCH$_3$ (See Preparation number 22) |
| 5.15 | Des N100 | 85 | 15 |
| | | | Mole percent HFPO—C(O)NHCH$_2$CH$_2$OH (MW 938.5) |
| 5.16 | Des N100 | 85 | 15 |
| 5.17 | Des N100 | 75 | 25 |
| | | | Mole percent HFPO—C(O)NHCH$_2$CH$_2$OH (MW 1547.2) |
| 5.18 | Des N100 | 85 | 15 |
| 5.19 | Des N100 | 75 | 25 |

Preparation No. 6. Preparation of Des N100/0.90 PET3A/0.15 HFPO

A 500 ml roundbottom 2-necked flask equipped with magnetic stir bar was charged with 25.00 g (0.131 eq, 191 EW) Des N100, 26.39 g (0.0196 eq, 1344 EW) F(CF(CF$_3$)CF$_2$O)$_{6.85}$ CF(CF$_3$)C(O)NHCH$_2$CH$_2$OH, and 109.62 g MEK, and was swirled to produce a homogeneous solution. The flask was placed in an 80 degrees Celsius bath, charged with 2 drops of dibutyltin dilaurate catalyst, and fitted with a condenser. The reaction was cloudy at first, but cleared within two minutes. At about 1.75 hours, the flask was removed from the bath and 2.42 g of MEK was added to compensate for lost solvent. A 2.0 g sample was removed from the flask, leaving (1-(2.0/161.01) or 0.9876 weight fraction, of the reaction, and 57.51 g (98.76% of 58.23 g) (0.116 mol, 494.3 equivalent weight) PET3A was added to the reaction, which was placed in a 63 degrees Celsius bath. At about 5.25 hours FTIR showed no isocyanate absorption at 2273 cm$^{-1}$, and 0.56 g MEK was added to compensate for solvent lost to bring the material to 50% solids. The product has a calculated wt % F of 15.6%).

Preparation No. 7. Preparation of Des N100/0.90 HEA/0.10 HFPO

By a procedure similar to that for Preparation 5.1 shown in Table 1 above, 28.34 g (0.1484 eq) Des N100, 19.94 g (0.148 eq) F(CF(CF$_3$) CF$_2$O)$_{6.85}$ CF(CF$_3$)C(O)NHCH$_2$CH$_2$OH, in 63.8 g MEK, with 2 drops of DBTDL, 0.03 g BHT were reacted for 1 hour, followed by addition of 15.51 g (0.1336 eq) HEA to provide, after reaction overnight, the desired material.

Preparation No. 8. Preparation of Des N100/ HFPO—C(O)NHCH$_2$CH$_2$OH/MeFBSE/PET3A (in 30/10/10/10 ratio)

A 120 ml bottle was charged with 5.73 g Des N100 (EW about 191, about 30 milliequivalents NCO), 3.57 g MeFBSE (MW=357, 10 milliequivalents OH), 13.44 g HFPO—C(O)NHCH$_2$CH$_2$OH (MW about 1344, 10 milliequivalents OH), 4.94 g PET3A (EW about 494.3, about 10 milliequivalents OH), 5 drops of dibutyltin dilaurate catalyst and 42 g MEK (about 40% solid) under nitrogen. The solution was reacted at 70 degrees Celsius in an oil bath with a magnetic stir bar for 20 hours after sealing the bottle. A clear solution was obtained after reaction, which showed no unreacted —NCO signal in FTIR analysis.

Preparation No. 9. Preparation of Des N100/ HFPO—C(O)NHCH$_2$CH$_2$OH/MeFBSE/PET3A (in 40/10/10/20 ratio)

A 120 ml bottle was charged with 7.64 g Des N100 (EW about 191, about 40 milliequivalents NCO), 3.57 g MeFBSE (MW=357, 10 milliequivalents OH), 13.44 g HFPO—C(O)NHCH$_2$CH$_2$OH (MW about 1344, 10 milliequivalents OH), 9.89 g PET3A (EW about 494.3, about 20 milliequivalents OH), 5 drops of dibutyltin dilaurate catalyst and 52 g MEK (about 40% solid) under nitrogen. The solution was reacted at 70 degrees Celsius in an oil bath with a magnetic stir bar for 20 hours after sealing the bottle. A clear solution was obtained after reaction, which showed no unreacted —NCO signal in FTIR analysis.

Preparation No. 10. Preparation of Des 100/ C$_6$F$_{13}$C$_2$H$_4$OH/PET3A (in 20/10/10 ratio)

A 120 ml bottle was charged with 3.82 g Des N100 (EW about 191, about 20 milliequivalents NCO), 3.64 g C$_6$F$_{13}$C$_2$H$_4$OH (MW=363, 10 milliequivalents OH), 4.94 g PET3A (EW about 494.3, about 10 milliequivalents OH), 3 drops of dibutyltin dilaurate catalyst and 19 g MEK (about 40% solid) under nitrogen. The solution was reacted at 70 degrees Celsius in an oil bath with a magnetic stir bar for 20 hours after sealing the bottle. A clear solution was obtained after reaction, which showed no unreacted —NCO signal in FTIR analysis.

Preparation No. 11. Preparation of Des 100/HO (CH$_2$)$_{10}$OH/HFPO—C(O)NHCH$_2$CH$_2$OH/PET3A (in 60/20/15/25 ratio)

A 120 ml bottle was charged with 11.46 g Des N100 (EW about 191, about 60 milliequivalents NCO), 1.74 g HO(CH$_2$)$_{10}$OH (MW=174, 20 milliequivalents OH), 20.16 g HFPO—C(O)NHCH$_2$CH$_2$OH (MW about 1344, 15 milliequivalents OH), 12.36 g PET3A (EW about 494.3, about 25 milliequivalents OH), 5 drops of dibutyltin dilaurate catalyst and 106 g MEK (about 30% solid) under nitrogen. The solution was reacted at 70 degrees Celsius in an oil bath with a magnetic stir bar for 20 hours after sealing the bottle. A clear solution was obtained after reaction, which showed no unreacted —NCO signal in FTIR analysis.

Preparation No. 12. Preparation of Des N100/FB-SEE/HFPO—C(O)NHCH$_2$CH$_2$OH/PET3A (in 30/10/7.5/12.5 ratio)

A 120 ml bottle was charged with 5.73 g Des N100 (EW about 191, about 30 milliequivalents NCO), 1.94 g FBSEE (MW=387, 10 milliequivalents OH), 10.08 g HFPO—C(O)NHCH$_2$CH$_2$OH (MW about 1344, 7.5 milliequivalents OH), 6.18 g PET3A (EW about 494.3, about 12.5 milliequivalents OH), 5 drops of dibutyltin dilaurate catalyst and 56 g MEK (about 30% solid) under nitrogen. The solution was reacted at 70 degrees Celsius in an oil bath with a magnetic stir bar for 20 hours after sealing the bottle. A clear solution was obtained after reaction, which showed no unreacted —NCO signal in FTIR analysis.

Preparation No. 13. Preparation of Des N3300/HFPODO/PET3A (in 30/10/20 ratio)

A 240 ml bottle was charged with 5.79 g Des N3300 (EW about 193, about 30 milliequivalents NCO), 6.71 g HFPODO (MW about 1341, 10 milliequivalents OH), 9.89 g PET3A (EW about 494.3, about 20 milliequivalents OH), 5 drops of dibutyltin dilaurate catalyst and 52 g MEK (about 30% solid) under nitrogen. The solution was reacted at 70 degrees Celsius in an oil bath with a magnetic stir bar for 10 hours after sealing the bottle. There was a small amount of precipitate formed upon standing at room temperature. FTIR analysis showed no unreacted —NCO signal.

Preparation No. 14. Preparation of Des N3300/HFPODO/HFPO—C(O)NHCH$_2$CH$_2$OH/PET3A (in 30/10/5/15 ratio)

A 240 ml bottle was charged with 5.79 g Des N3300 (EW about 193, about 30 milliequivalents NCO), 6.71 g HFPODO (MW about 1341, 10 milliequivalents OH), 6.72 g HFPO—C(O)NHCH$_2$CH$_2$OH (MW about 1344, 5 milliequivalents OH), 7.42 g PET3A (EW about 494.3, about 15 milliequivalents OH), 5 drops of dibutyltin dilaurate catalyst, 27 g MEK and 10 g C$_4$F$_9$OCH$_3$ (about 20% solid) under nitrogen. The solution was reacted at 70 degrees Celsius in an oil bath with a magnetic stir bar for 10 hours after sealing the bottle. Separation into two liquid phases occurred upon standing at room temperature. Addition of more C$_4$F$_9$OCH$_3$ produced a clear homogeneous solution at about 17% solids. FTIR analysis showed no unreacted —NCO signal.

Preparation No. 15. Preparation of Des N3300/HFPODO/MeFBSE/PET3A (in 30/10/5/15 ratio)

A 120 ml bottle was charged with 5.79 g Des N3300 (EW about 191, about 30 milliequivalents NCO), 6.71 g HFPODO (MW about 1341, 10 milliequivalents OH), 1.79 g MeFBSE (MW=357, 5 milliequivalents OH), 7.42 g PET3A (EW about 494.3, about 15 milliequivalents OH), 5 drops of dibutyltin dilaurate catalyst and 51 g MEK (about 30% solid) under nitrogen. The solution was reacted at 70 degrees Celsius in an oil bath with a magnetic stir bar for 10 hours after sealing the bottle. A clear solution was obtained at 70 degrees Celsius after reaction, but there was a small amount of precipitate formed upon standing at room temperature. FTIR analysis showed no unreacted —NCO signal.

Preparation No. 16. Preparation of Des N3300/Fox-Diol/HFPO—C(O)NHCH$_2$CH$_2$OH/PET3A (in 30/10/5/15 ratio)

A 240 ml bottle was charged with 5.79 g Des N3300 (EW about 191, about 30 milliequivalents NCO), 6.71 g Fox-Diol (MW about 1341, 10 milliequivalents OH), 6.72 g HFPO—C(O)NHCH$_2$CH$_2$OH (MW about 1344, 5 milliequivalents OH), 7.40 g PET3A (EW about 494.3, about 15 milliequivalents OH), 5 drops of dibutyltin dilaurate catalyst, 56 g MEK and 50 g C$_4$F$_9$OCH$_3$ (about 19% solid) under nitrogen. The solution was reacted at 70 degrees Celsius in an oil bath with a magnetic stir bar for 10 hours after sealing the bottle. A clear solution was obtained after reaction. FTIR analysis showed no unreacted —NCO signal.

Preparation No. 17. Preparation of Des N3300/Fomblin Zdol/PET3A (in 30/10/20 ratio)

A 240 ml bottle was charged with 5.79 g Des N3300 (EW about 191, about 30 milliequivalents NCO), 10.0 g Fomblin Zdol (MW about 2000, 10 milliequivalents OH), 9.89 g PET3A (EW about 494.3, about 20 milliequivalents OH), 5 drops of dibutyltin dilaurate catalyst, 63 g MEK and 40 g C$_4$F$_9$OCH$_3$ (about 18% solid) under nitrogen. The solution was reacted at 70 degrees Celsius in an oil bath with a magnetic stir bar for 10 hours after sealing the bottle. A clear solution was obtained after reaction. FTIR analysis showed no unreacted —NCO signal.

Preparation No. 18. Preparation of Des N3300/HHA/HFPO—C(O)NHCH$_2$CH$_2$OH/PET3A (in 30/10/10/10 ratio)

A 240 ml bottle was charged with 5.79 g Des N3300 (EW about 191, about 30 milliequivalents NCO), 6.14 g HHA (MW about 1228, 10 milliequivalents OH), 12.29 g HFPO—C(O)NHCH$_2$CH$_2$OH (MW about 1229, 10 milliequivalents OH), 4.93 g PET3A (EW about 494.3, about 10 milliequivalents OH), 5 drops of dibutyltin dilaurate catalyst, 85 g MEK and 25 g C$_4$F$_9$OCH$_3$ (about 20% solid) under nitrogen. The solution was reacted at 70 degrees Celsius in an oil bath with a magnetic stir bar for 10 hours after sealing the bottle. A clear solution was obtained after reaction. FTIR analysis showed no unreacted —NCO signal.

Preparation No. 19. Preparation of PAPI/HFPO—C(O)NHCH$_2$CH$_2$OH/PET3A (in 28/8/20 ratio)

A 120 ml bottle was charged with 3.75 g PAPI (EW about 134, about 28 milliequivalents NCO), 10.75 g HFPO—C(O)NHCH$_2$CH$_2$OH (MW about 1344, 8 milliequivalents OH), 9.88 g PET3A (EW about 494.3, about 20 milliequivalents OH), 5 drops of dibutyltin dilaurate catalyst and 37 g MEK (about 40% solid) under nitrogen. The solution was reacted at 70 degrees Celsius in an oil bath with a magnetic stir bar for 5 hours after sealing the bottle. A clear solution was obtained after reaction. FTIR analysis showed no unreacted —NCO.

D. General Preparation of Perfluoropolyether Urethane Multiacrylates Containing Trialkoxysilane Functionality Preparation No. 20. Preparation of Des N100/0.75 PET3A/0.15 HFPO/0.15H$_2$N(CH$_2$)$_3$Si(OCH$_3$)$_3$ A 500 ml roundbottom flask equipped with stir bar was charged with 25.00 g (0.1309 eq) Des N100, 103.43 g MEK, 2 drops of DBTDL, 26.39 g (0.0196 eq) HFPO—C(O)NHCH$_2$CH$_2$OH, 1344 equivalent weight, and 0.05 g BHT, and placed in a 60 degrees Celsius oil bath. After 1 hour, 3.52 g (0.0196 eq) H$_2$N(CH$_2$)$_3$Si(OCH$_3$)$_3$ was added, followed in 10 minutes by the addition of 48.52 g (0.0982 eq, 494.3 equivalent weight) SR444c. The reaction mixture showed no residual isocyanate by FTIR after a total reaction time of 5.75 hours.

The preparation of other perfluoropolyether urethane multiacrylates containing trialkoxysilane functionality was done by a similar procedure, substituting the appropriate amounts of materials, and are summarized in Table 2 as Preparation Nos. 20.1 through 20.4:

TABLE 2

| Preparation Number | Isocyanate used (set at 100 Mole percent NCO in all cases) | Mole percent PET3A | Mole percent HFPO—C(O)NHCH$_2$CH$_2$OH | Mole percent H$_2$N(CH$_2$)$_3$•Si(OCH$_3$)$_3$ |
|---|---|---|---|---|
| 20.1 | Des N100 | 75 | 15 | 15 |
| 20.2 | Des N100 | 60 | 15 | 30 |
| 20.3 | Des N100 | 45 | 15 | 45 |
| 20.4 | Des N100 | 30 | 15 | 60 |

Preparation No. 21. Preparation of Des N3300/ HFPO—C(O)NHCH$_2$CH$_2$OH/HSC$_3$H$_6$Si(OCH$_3$)$_3$/ PET3A (in 30/8/2/20 ratio)

A 240 ml bottle was charged with 5.79 g Des N3300 (EW about 193, about 30 milliequivalents NCO), 9.83 g HFPO—C(O)NHCH$_2$CH$_2$OH (MW about 1229, 8 milliequivalents OH), 0.39 g HSC$_3$H$_6$Si(OMe)$_3$ (MW=196, 2 milliequivalents SH), 5 drops of dibutyltin dilaurate catalyst, 40 g MEK and 20 g C$_4$F$_9$OCH$_3$ under nitrogen. The solution was reacted at 70 degrees Celsius in an oil bath with a magnetic stir bar for 2 hours after sealing the bottle. Then, 4.46 g PET3A (EW about 494.3, about 20 milliequivalents OH) was added at room temperature under nitrogen. The solution was allowed to react for another 6 hours at 70 degrees Celsius. A clear solution was obtained after reaction, which showed no unreacted —NCO signal in FTIR analysis.

Preparation No. 22. Preparation of HFPO—C(O) NHCH$_2$CH$_2$CH$_2$NHCH$_3$ Starting material A 1-liter round-bottom flask was charged with 291.24 g (0.2405 mol) of HFPO—C(O)OCH$_3$ and 21.2 g (0.2405 mol) N-methyl-1,3-propanediamine, both at room temperature, resulting in a cloudy solution. The flask was swirled and the temperature of the mixture rose to 45 degrees Celsius, and to give a water-white liquid, which was heated overnight at 55 degrees Celsius. The product was then placed on a rotary evaporator at 75 degrees Celsius and 28 inches of Hg vacuum to remove methanol, yielding 301.88 g of a viscous slightly yellow liquid, nominal molecular weight is equal to 1267.15 g/mol.

Preparation No. 23. Preparation of HFPO—C(O) NHC(CH$_2$CH$_3$)(CH$_2$C(=O)NHC$_2$H$_4$OC(O)C(CH$_3$) =CH$_2$)$_2$ A 240 ml bottle was charged with 6.49 g HFPO—C(O) NHC(CH$_2$CH$_3$)(CH$_2$OH)$_2$ (1298.5 MW, 5 mmol) ("Preparation No. 3"), 1.55 g IEM (OCNC$_2$H$_4$OC(O)C(CH$_3$)=CH$_2$, MW=155, 10 mmol), 3 drops of dibutyltin dilaurate catalyst, 50 mg BHT, 32 g ethyl acetate and 10 g C$_4$F$_9$OCH$_3$. The solution was reacted at 70 degrees Celsius in an oil bath with a magnetic stir bar for 8 hours after sealing the bottle. A clear solution was obtained after reaction, which showed no unreacted —NCO by in FTIR analysis, providing a solution of the product HFPO—C(O)NHC(CH$_2$CH$_3$)(CH$_2$C(=O) NHC$_2$H$_4$OC(O)C(CH$_3$)=CH$_2$)$_2$.

Preparation No. 24. Preparation of HFPO—C(O) NHCH$_2$CH$_2$O C(=O)NHC$_2$H$_4$OC(O)C(CH$_3$) =CH$_2$) (HFPO-IEM)

A 120 ml bottle was charged with 71.20 g (MW ~1229, 57.9 mmol) HFPO—C(O)NHC$_2$H$_4$OH, 9.0 g of CH$_2$=C (CH$_3$)CO$_2$C$_2$H$_4$NCO (MW=155, 58 mmol), 52 g EtOAc, 3 drops of DBTDL and 1.5 mg of phenothiazine under nitrogen. The solution was heated in a oil bath at 70 degrees Celsius for 6 hours with a magnetic stirring after sealing the bottle. Fourier Transform Infrared Spectroscopy (FTIR) analysis indicated no remaining isocyanate.

Preparation No. 25. Preparation of HFPO—C(O)N (H)CH$_2$CH(OC(O)CH=CH$_2$)CH$_2$OC(O)CH=CH$_2$ The title material was prepared as described in U.S. Patent Application Publication No. 2005/0249940, referred to as FC-4 and had a calculated wt-% fluorine of 58.5%.

Preparation No. 26. Preparation of CH$_3$(O)CCF(CF$_3$) (OCF$_2$CF(CF$_3$)$_b$OCF$_2$CF$_2$CF$_2$CF$_2$O(CF(CF$_3$)CF$_2$ O)$_c$CF (CF$_3$)COOCH$_3$(H$_3$CO(O)C—HFPO—C(O)OCH$_3$)H$_3$CO (O)C—HFPO—C(O)OCH$_3$, in which b+c average about 4.5 can be prepared using FC(O)CF$_2$CF$_2$C(O)F as an initiator according to the method reported in U.S. Pat. No. 3,250,807 (Fritz, et al.) which provides the HFPO oligomer bis-acid fluoride, followed by methanolysis and purification by removal of lower boiling materials by fractional distillation as described in U.S. Pat. No. 6,923,921 (Flynn, et. al.). The disclosure of both aforementioned patents are incorporated herein by reference.

Preparation No. 27. Preparation of HOCH$_2$CH$_2$N(H) (O)C—HFPO—C(O)N(H)CH$_2$CH$_2$OH A 200 ml roundbottom flask equipped with magnetic stirbar was charged with 3.81 g (0.0624 mol) ethanolamine and heated to 75 degrees Celsius under a dry air. A charge of 30.0 g (0.240 mol, 1250 MW) H$_3$CO(O)C—HFPO—C(O)OCH$_3$ was added via a pressure equalizing funnel over 40 min and the reaction was allowed to heat for about 18 h. From Fourier Transform Infrared Spectroscopy (FTIR) analysis, the amide —C(O)NH— was formed as the ester signal (—CO$_2$—) disappeared. Next 50.7 g of methyl t-butyl ether was added to the reaction to provide a solution that was washed successively with 20 ml of 2N aqueous HCl, and then 3 times with 20 ml of water, The solution was then dried over anhydrous magnesium sulfate, filtered and concentrated on a rotary evaporator at aspirator pressure in a 75 degrees Celsius water bath to provide the product as a thick syrup.

Preparation No. 28. Preparation of H$_2$C=CHC(O) OCH$_2$CH$_2$N(H)(O)C—HFPO—C(O)N(H) CH$_2$CH$_2$OC(O)CH=CH$_2$ A 500 ml roundbottom equipped with stirbar was charged with 40.00 g (0.0306 mol, 1308.6 MW) HOCH$_2$CH$_2$N(H)(O) C—HFPO—C(O)N(H)CH$_2$CH$_2$OH, 6.64 g (0.0734 mol) triethylamine, and 54.36 g MTBE and heated at 40 degrees Celsius. A charge of 6.64 g (0.734 mol) of acryloyl chloride was added via pressure equalizing funnel over about 30 min, and the reaction was allowed to heat for about 18 h. The reaction was washed with 40 g 1N HCl, with addition of 60 g of brine and 60 g of MTBE, followed by a wash with 50 g of 5% aqueous sodium carbonate and 50 g of brine, and was finally dried over anhydrous magnesium sulfate, filtered and concentrated on a rotary evaporator at aspirator pressure in a 75 degrees Celsius water bath to provide the product as a thick syrup. It has a calculated wt-% fluorine of 58.1%.

Preparation No. 29. Preparation of $(HOCH_2)_2$ $CH_3CH_2CN(H)(O)C$—$HFPO$—$C(O)N(H)CCH_2CH_3$ $(CH_2OH)_2$ In a manner similar to the preparation of 27, 65.00 g (0.520 mol) $H_3CO(O)C$—$HFPO$—$C(O)OCH_3$, was reacted with 16.11 g (0.1352 mol) 2-amino-2-ethyl-1,3-propanediol to provide after the desired product as a thick slightly yellow syrup.

Preparation No. 30. Preparation of $(H_2C=CHC$ $(OOCH_2)_2CH_3CH_2CN(H)(O)C$—$HFPOC(O)N(H)$ $CCH_2CH_3(CH_2OC(O)CH=CH_2)_2$ In a manner similar to the preparation no. 28, 10.00 g (0.0067 mol, 1488.3 MW) was dissolved in 16.31 g MTBE and 3.39 g (0.0336 mol) triethylamine, and reacted at 40 degrees Celsius with 2.92 g (0.0323 mol) acryloyl chloride, to provide after workup and chromatographic purification (using 33/67 ethyl acetate/hexane (volume/volume) on a Analogix IF 280 Flash chromatography workstation (Analogix, Inc., Burlington, Wis.) using a SF40-150 Superflash™ column) the desired product. It has a calculated wt-% fluorine of 50.1%.

Preparation 31a

HFPO-AEA ($HFPO$—$C(O)NHCH_2CH_2OC(O)$ $CH=CH_2$) was prepared as described in U.S. Pat. No. 7,101, 618; under Preparation of Monofunctional Perfluoropolyether Acrylate (FC-1). It has a calculated wt % F of 62.5%.

Preparation 31b. Synthesis of HFPO-EO3-A was prepared in a manner similar to HFPO-AEA 31a except the HFPO-amidol, 4b (HFPO-EO3-OH) was used in place of 4a. It has a calculated wt % F of 59.1%.

Preparation 31c. Synthesis of HFPO-EO4-A was prepared in a manner similar to HFPO-AEA 31a except the HFPO-amidol, 4c (HFPO-EO4-OH) was used in place of 4a. It has a calculated wt % F of 57.4%.

Preparation 31d. Synthesis of HFPO-AH-A was prepared in a manner similar to HFPO-AEA 31a except the HFPO-amidol, 4d (HFPO-AH-OH) was used in place of 4a. It has a calculated wt % F of 60.4%.

E. Test Methods

Steel Wool Testing: The abrasion resistance of the cured films was tested cross-web to the coating direction by use of a mechanical device capable of oscillating cheesecloth or steel wool fastened to a stylus (by means of a rubber gasket) across the film's surface. The stylus oscillated over a 10 cm wide sweep width at a rate of 3.5 wipes/second wherein a "wipe" is defined as a single travel of 10 cm. The stylus had a flat, cylindrical geometry with a diameter of 1.25 inch (3.2 cm). The device was equipped with a platform on which weights were placed to increase the force exerted by the stylus normal to the film's surface. The cheesecloth was obtained from Summers Optical, EMS Packaging, a subdivision of EMS Acquisition Corp., Hatfield, Pa. under the trade designation "Mil Spec CCC-c-440 Product #S 12905". The cheesecloth was folded into 12 layers. The steel wool was obtained from Rhodes-American, a division of Homax Products, Bellingham, Wash. under the trade designation "#0000-Super-Fine" and was used as received. A single sample was tested for each example, with the weight in grams applied to the stylus and the number of wipes employed during testing reported.

Taber Testing: The Taber test was run according to ASTM D1044-99 using CS-10 wheels.

Contact Angle: The coatings were rinsed for 1 minute by hand agitation in IPA before being subjected to measurement of water and hexadecane contact angles. Measurements were made using as-received reagent-grade hexadecane (Aldrich) and deionized water filtered through a filtration system obtained from Millipore Corporation (Billerica, Mass.), on a video contact angle analyzer available as product number VCA-2500XE from AST Products (Billerica, Mass.). Reported values are the averages of measurements on at least three drops measured on the right and the left sides of the drops. Drop volumes were 5 µL for static measurements and 1-3 µL for advancing and receding. For hexadecane, only advancing and receding contact angles are reported because static and advancing values were found to be nearly equal.

Surface Smoothness (Dewetting): For some of the tables below, a visual inspection was made regarding the smoothness of the applied dry film. While the measurement of smoothness by visual inspection is a subjective determination, a smooth film, for the purposes of the present invention, is deemed to be a surface layer that is substantially continuous and free of visible defects in reflected light as observed by visual observation of the coating surface at a wide variety of possible angles. Typically, visual observation is accomplished by looking at the reflection of a light source from the coating surface at an angle of about 60 degrees from perpendicular. Visual defects that may be observed include but are not limited to pock marks, fish eyes, mottle, lumps or substantial waviness, or other visual indicators known to one of ordinary skill in the art in the optics and coating fields. Thus, a "rough" surface as described below has one or more of these characteristics, and may be indicative of a coating material in which one or more components of the composition are incompatible with each other. Conversely, a substantially smooth coating, characterized below as "smooth" for the purpose of the present invention, presumes to have a coating composition in which the various components, in the reacted final state, form a coating in which the components are compatible or have been modified to be compatible with one another and further has little, if any, of the characteristics of a "rough" surface.

The surfaces may also be classified for dewetting as "good," "very slight" (v.sl), "slight" (sl), "fair," or "poor." A "good" surface meaning a substantially smooth surface having little dewetting. A "very slight," "slight", or "fair" categorization means that the surface has an increasing portion of defects but is still substantially acceptable for smoothness. A "poor" surface has a substantial amount of defects, indicating a rough surface that has a substantial amount of dewetting.

Durability of Ink Repellency was assessed using a modified Oscillating Sand Method (ASTM F 735-94). An orbital shaker was used (VWR DS-500E, from VWR Bristol, Conn.). A disk of diameter 89 mm was cut from the sample, placed in a 16 ounce jar lid (jar W216922 from Wheaton, Millville, N.J.), and covered with 50 grams of 20-30 mesh Ottawa sand (VWR, Bristol, Conn.). The jar was capped and placed in the shaker set at 300 rpm for 15 minutes. After shaking, a Sharpie permanent marker was used to draw a line across the diameter of the disk surface. The portion of the ink line that did not bead up was measured. A measure of 89 mm is equal to 100% ink repellency loss; a measure of 0 mm would be perfect durability or 0% ink repellency (IR) loss.

F. Experiments

The ceramer hardcoat ("HC-1") used in the examples was made as described in column 10, line 25-39 and Example 1 of U.S. Pat. No. 5,677,050 to Bilkadi, et al.

Experiment 1

Solutions as generally described in Tables 3-5 below were prepared at 30% solids in a solvent blend of 1:1 isopropanol: ethyl acetate and coated at a dry thickness of about 4 microns using a number 9 wire wound rod onto 5-mil Melinex 618 film. The coatings were dried in an 80 degree Celsius oven for 1 minute and then placed on a conveyer belt coupled to a ultraviolet ("UV") light curing device and UV cured under nitrogen using a Fusion 500 watt H bulb at 20 ft/min. The values reported in the Tables refer to the percent solids of each component of the dried coating. The coatings were then visually inspected for surface smoothness (dewetting). The coatings were also tested for durability of ink repellency. Results are shown in Tables 3 and 4.

TABLE 3

| Percentage HC-1 in coating | Preparation number | Percentage Preparation in coating | Dewet | Ink Repel. |
|---|---|---|---|---|
| 99.9 | 5.5 | 0.1 | good | 65 |
| 99.8 | 5.5 | 0.2 | v.sl | 53 |
| 99.7 | 5.5 | 0.3 | fair | 49 |
| 99.86 | 5.4 | 0.14 | sl | 51 |
| 99.72 | 5.4 | 0.28 | sl | 44 |
| 99.58 | 5.4 | 0.42 | sl | 40 |
| 99.7 | 5.3 | 0.3 | good | 35 |
| 99.4 | 5.3 | 0.6 | v.sl | 34 |
| 99.1 | 5.3 | 0.9 | sl | 31 |
| 99.9 | 5.11 | 0.1 | good | 65 |
| 99.8 | 5.11 | 0.2 | v.sl | 49 |
| 99.7 | 5.11 | 0.3 | sl | 50 |
| 99.86 | 5.10 | 0.14 | good | 60 |
| 99.72 | 5.10 | 0.28 | good | 37 |
| 99.58 | 5.10 | 0.42 | v.sl | 38 |
| 99.7 | 5.9 | 0.3 | good | 42 |
| 99.4 | 5.9 | 0.6 | good | 43 |
| 99.1 | 5.9 | 0.9 | v.sl | 47 |

Selected coatings, before sand testing, from another coating run were analyzed for contact angles and the results are shown in Table 4.

TABLE 4

| Preparation Number | Wt % in HC-1 | Water static/ Adv/Rec CA (deg) | Hexadecane Adv/Rec CA (deg) |
|---|---|---|---|
| 5.3 | 0.3 | 108/119/91 | 71/65 |
| 5.3 | 0.6 | 109/120/90 | 72/67 |
| 5.5 | 1.2 | 108/120/90 | 73/67 |
| 5.9 | 1.2 | 109/121/89 | 74/67 |
| 4.11 | 1.2 | 108/118/85 | 74/64 |

Another set of examples was run according to the same procedure as examples in Table 1. The results are shown in Table 5.

TABLE 5

| Percentage HC-1 in coating | Preparation number | Percentage Preparation in coating | Smoothness | Ink Repellency |
|---|---|---|---|---|
| 99.8 | 5.3 | 0.2 | good | 32 |
| 99.7 | 5.3 | 0.3 | good | 22 |
| 99.6 | 5.3 | 0.4 | v.sl | 23 |
| 99.76 | 5.2 | 0.24 | good | 46 |
| 99.52 | 5.2 | 0.48 | good | 26 |
| 99.33 | 5.2 | 0.67 | good | 42 |
| 99.8 | 5.10 | 0.2 | good | 25 |
| 99.7 | 5.10 | 0.3 | good | 42 |
| 99.6 | 5.10 | 0.4 | v.sl | 42 |
| 99.64 | 5.9 | 0.36 | good | 26 |
| 99.43 | 5.9 | 0.57 | good | 12 |
| 99.22 | 5.9 | 0.78 | good | 33 |
| 99.76 | 5.8 | 0.24 | good | 47 |
| 99.52 | 5.8 | 0.48 | good | 18 |
| 99.33 | 5.8 | 0.67 | v.sl | 33 |

Table 6 shows the results of another set of examples that was run at two levels of additives in an HC-1 hardcoat in which the sand test was run for 25 minutes at 300 rpm. The examples were run according to the same procedure as examples in Table 1 described above.

TABLE 6

| Percentage HC-1 in coating | Preparation number | Percentage Preparation in coating | Smoothness | Ink Repellency |
|---|---|---|---|---|
| 99.8 | 9 | 0.2 | sl | 20 |
| 99.0 | 9 | 1.0 | sl | 10 |
| 99.8 | 8 | 0.2 | good | 29 |
| 99.0 | 8 | 1.0 | poor | 25 |
| 99.8 | 10 | 0.2 | good | 38 |
| 99.0 | 10 | 1.0 | good | 30 |
| 99.8 | 11 | 0.2 | good | 40 |
| 99.0 | 11 | 1.0 | fair | 20 |
| 99.8 | 12 | 0.2 | good | 36 |
| 99.0 | 12 | 1.0 | poor | 22 |
| 99.8 | 19 | 0.2 | good | 20 |
| 99.0 | 19 | 1.0 | sl | 49 |
| 99.8 | 5.2 | 0.2 | good | 5 |

Table 7 shows the results of another set of examples that was run at two levels of additives in an HC-1 hardcoat in which the sand test was run for 25 minutes at 300 rpm and in a separate set for 35 minutes at 300 rpm. The examples were run according to the same procedure as examples in Table 1 described above.

TABLE 7

| % HC-1 in coating | Preparation number | Percentage Preparation in coating | Smoothness | Ink Repellency 25 min at 300 rpm | Ink Repellency 35 min at 300 rpm |
|---|---|---|---|---|---|
| 99.5 | 5.2 | 0.5 | good | 0 | |
| 99.5 | 5.2 | 0.5 | good | | 10 |
| 99.8 | 5.1 | 0.2 | good | 35 | |
| 99.0 | 5.1 | 1.0 | good | 0 | |
| 99.0 | 5.1 | 1.0 | good | | 36 |
| 99.8 | 5.6 | 0.2 | sl | 0 | |
| 99.0 | 5.6 | 1.0 | poor | 0 | |
| 99.8 | 5.7 | 0.2 | poor | 62 | |
| 99.0 | 5.7 | 1.0 | poor | 26 | |
| 99.8 | 5.12 | 0.2 | good | 0 | |

TABLE 7-continued

| % HC-1 in coating | Preparation number | Percentage Preparation in coating | Smoothness | Ink Repellency 25 min at 300 rpm | Ink Repellency 35 min at 300 rpm |
|---|---|---|---|---|---|
| 99.0 | 5.12 | 1.0 | fair | 0 | |
| 99.8 | 5.12 | 0.2 | good | | 54 |
| 99.8 | 5.13 | 0.2 | good | 0 | |
| 99.0 | 5.13 | 1.0 | good | 0 | |
| 99.0 | 5.13 | 1.0 | good | | 38 |
| 99.8 | 5.14 | 0.2 | good | 0 | |
| 99.0 | 5.14 | 1.0 | good | 0 | |
| 99.0 | 5.14 | 1.0 | good | | 35 |
| 99.8 | 5.15 | 0.2 | good | 5 | |
| 99.0 | 5.15 | 1.0 | good | 0 | |
| 99.0 | 5.15 | 1.0 | slight | | 11 |
| 99.8 | 5.3 | 0.2 | good | 0 | |
| 99.2 | 5.3 | 1.0 | sl | 0 | |
| 99.5 | 5.3 | 0.5 | good | | 25 |
| 99.8 | 5.16 | 0.2 | good | 10 | |
| 99.0 | 5.16 | 1.0 | good | 0 | |
| 99.0 | 5.16 | 1.0 | good | | 38 |
| 99.8 | 5.17 | 0.2 | good | 0 | |
| 99.0 | 5.17 | 1.0 | v.sl | 0 | |
| 99.5 | 5.17 | 0.5 | good | | 25 |
| 99.8 | 5.18 | 0.2 | good | 0 | |
| 99.0 | 5.18 | 1.0 | sl | 0 | |
| 99.8 | 5.18 | 0.2 | good | | 47 |
| 99.8 | 5.19 | 0.2 | good | 0 | |
| 99.0 | 5.19 | 1.0 | sl | 0 | |
| 99.8 | 5.19 | 0.2 | sl | | 36 |
| 99.8 | 8 | 0.2 | good | | 27 |
| 98.5 | 10 | 1.5 | good | | 30 |

An example set illustrating the use of perfluoropolyether diols in the invention was run according to the same procedure as examples in Table 1. These results are shown in Table 8.

TABLE 8

| % HC-1 in coating | Preparation Number | Percentage Preparation in coating | Smoothness | Ink repellency 35 min at 300 rpm | Ink repellency 55 min at 300 rpm |
|---|---|---|---|---|---|
| 98.8 | 13 | 0.2 | good | 37 | |
| 99.0 | 13 | 1.0 | v.sl | 27 | |
| 99.5 | 14 | 0.5 | v.sl | 0 | 26 |
| 99.8 | 15 | 0.2 | good | 34 | |
| 99.0 | 15 | 1.0 | v.sl | 31 | |
| 99.8 | 16 | 0.2 | good | 0 | 28 |
| 99.0 | 16 | 1.0 | good | 0 | 26 |
| 99.8 | 17 | 0.2 | good | 26 | |
| 99.0 | 17 | 1.0 | v.sl | 34 | |

Another set illustrating the use of a multi acrylate diol in the invention, and a thiol functional trialkoxysilane was run according to the same procedure as examples in Table 1. These results are shown in Table 9.

TABLE 9

| Percentage HC-1 in coating | Preparation number | Percentage Preparation in coating | Smoothness | Ink repellency 40 min at 300 rpm |
|---|---|---|---|---|
| 99.3 | 18 | 0.7 | good | 32 |
| 99.3 | 21 | 0.7 | good | 40 |
| 99.3 | 4.2 | 0.7 | good | 0 |

An example set illustrating the trialkoxysilane functional perfluoropolyether urethane multiacrylates, a perfluoropolyether urethane acrylate made using hydroxyethyl acrylate, and a perfluoropolyether diol functionalized with isocyanatoethyl methacrylate was run according to the same procedure as examples in Table 1. These results are shown in Table 10.

TABLE 10

| Percentage HC-1 in coating | Preparation Number | Percentage Preparation in coating | Smoothness | Ink Repellency 20 min at 300 rpm |
|---|---|---|---|---|
| 99.6 | 20.1 | 0.4 | good | 0 |
| 99.6 | 20.2 | 0.4 | good | 0 |
| 99.6 | 20.3 | 0.4 | good | 0 |
| 99.6 | 20.4 | 0.4 | good | 0 |
| 99.6 | 7 | 0.4 | good | 0 |
| 99.6 | 23 | 0.4 | good | 0 |

A 30% solids (in a solvent blend of 1:1 isopropanol:ethyl acetate) sample of 99.4% PET4A/0.6% Des N100/0.85 PET3A/0.15 HFPO (Preparation 5.2) with 2% added Irgacure 907 was prepared. The solution was coated and cured by the same procedure as above. The smooth coating gave an ink repellency of 0 after a 20 minute sand test at 300 rpm.

Another set of examples using a perfluoropolyether alcohol functionalized with isocyanatoethyl methacrylate in combination with a compatibilizer was run according to the same procedure as examples in Table 1. The results are shown in Table 11.

TABLE 11

| Percentage HC-1 in coating | Preparation Number | Percentage Preparation in coating | Percentage FBSEA in coating | Smoothness | Ink Repellency 15 min. at 300 rpm |
|---|---|---|---|---|---|
| 99.7 | 24 | 0.03 | 0 | Dewet/rough | not run |
| 97.67 | 24 | 0.03 | 2.3 | good | 25 |
| 94.97 | 24 | 0.03 | 5 | good | 0 |
| 90.97 | 24 | 0.03 | 9 | good | 33 |
| 85.97 | 24 | 0.03 | 14 | good | 33 |

Another experiment was run in which HC-1 was applied to the 5-mil Melinex 618 film with a metered, precision die coating process. The hardcoat formulation with HC-1 and Des N100/0.85 PET3A/0.15 HFPO (Preparation 5.2) was diluted to 30 wt-% solids in isopropanol and coated onto the 5-mil PET backing to achieve a dry thickness of 5 microns. A flow meter was used to monitor and set the flow rate of the material from a pressurized container. The flow rate was adjusted by changing the air pressure inside the sealed container which forces liquid out through a tube, through a filter, the flow meter and then through the die. The dried and cured film was wound on a take up roll.

The coatings were dried in a 10-foot oven at 100 degrees Celsius, and cured with a 300-watt Fusion Systems H bulb at 100, 75, 50, and 25% power. The coating shown in Table 12 below was evaluated in a series of tests. The sand test was run for 15 minutes at 300 rpm. The Steel Wool Test was run checking for damage to the coating at 100, 250, 500, 750, and 1000 cycles. The results are summarized in Table 12. Contact angles were also run on selected samples before and after testing and these results are shown in Table 13.

TABLE 12

| Wt. % HC-1 in coating | (Preparation Number 5.2) Weight % in coating | UV dose % power | Ink repellency | Steel Wool (Cycles without scratches) | Taber testing % haze after 500 cycles | Taber testing Change in haze from initial value in % after 500 cycles |
|---|---|---|---|---|---|---|
| 99.27 | 0.73 | 100 | 0 | 1000 | 10.83 | 10.51 |
| 99.27 | 0.73 | 75 | 0 | 1000 | 8.38 | 8.04 |
| 99.27 | 0.73 | 50 | 0 | 1000 | 11.05 | 10.62 |
| 99.27 | 0.73 | 25 | 0 | 1000 | 8.35 | 8.04 |

Selected coatings from Table 12 were tested for contact angles with water and hexadecane, and are identified by the UV dose % power used in curing the coatings. The results are summarized in Table 13:

TABLE 13

| UV dose % power | Liquid used to test contact angle | Initial Advancing/ Static/Receding Contact angles | After Sand Testing Advancing/ Static/Receding Contact angles | After 1000 cycles - Steel Wool Advancing/ Static/Receding Contact angles |
|---|---|---|---|---|
| 100 | Water | 110/123/98 | 94/111/68 | 107/119/89 |
| 100 | Hexadecane | —/72/64 | —/61/49 | —/69/62 |
| 25 | Water | 107/120/84 | 91/105/53 | 103/118/72 |
| 25 | Hexadecane | —/71/62 | —/56/40 | —/63/55 |

Preparation of Hardcoat Substrate S1

A primed 5 mil transparent polyethylene terephthalate (PET) film was obtained from E.I. duPont de Nemours and Company, Wilmington, Del. under the trade designation "Melinex 618". A hardcoat composition substantially the same as Example 3 of U.S. Pat. No. 6,299,799 (HC-1) was coated onto the primed surface with a metered, precision die coating process. The hardcoat was diluted in IPA to 30 wt-% solids and coated onto the 5-mil PET backing to achieve a dry thickness of 5 microns. A flow meter was used to monitor and set the flow rate of the material from a pressurized container. The flow rate was adjusted by changing the air pressure inside the sealed container which forces liquid out through a tube, through a filter, the flow meter and then through the die. The dried and cured film was wound on a take up roll and used as the input backing Hardcoat Substrate S-1 for the coating solutions described below.

The hardcoat coating and drying parameters were as follows:

| Coating width: | 6" (15 cm) |
|---|---|
| Web Speed: | 30 feet (9.1 m) per minute |
| Solution % Solids: | 30.2% |
| Filter: | 2.5 micron absolute |
| Pressure Pot: | 1.5 gallon capacity (5.7l) |
| Flow rate: | 35 g/min |
| Wet Coating Thickness: | 24.9 microns |
| Dry Coating Thickness: | 4.9 microns |
| Conventional Oven Temps: | Zone 1 - 140° F. (60° C.) |
| | Zone 2 - 160° F. (53° C.) |
| | Zone 3 - 180° F. (82° C.) |

Each zone was 10 ft (3 m) in length.

The coating compositions described in Table 14 were coated onto the hardcoat layer S1 using a precision, metered die coater. For this step, a syringe pump was used to meter the solution into the die. The solutions were diluted with MEK to a concentration of 1% and coated onto the hardcoat layer to achieve a dry thickness of 60 nm. The material was dried in a conventional air flotation oven and then cured a 600 watt Fusion Systems bulb under nitrogen using the conditions show below:

| Coating width: | 4" (10 cm) |
|---|---|
| Web Speed: | 20 feet per minute |
| Solution % Solids: | 1.0% |
| Pump: | 60 cc Syringe Pump |
| Flow rate: | 1.2 cc/min |
| Wet Coating Thickness: | 4.1 microns |
| Dry Coating Thickness: | 60 nm |
| Conventional Oven Temps: | Zone 1 - 65° C. |
| | Zone 2 - 65° C.. |

Both zones at 10 ft (3 m) in length.

The coatings were made and tested for ink repellency before and after a sand test at 300 rpm for 15 min and for initial water static contact angle.

TABLE 14

| TMPTA (%) | HFPO- Urethane Preparation- 6(%) | HFPO- AEA (31a) | Darocur 1173 | % Ink Repellency loss | Static water Contact angle (range in degrees) |
|---|---|---|---|---|---|
| 95 | 3.75 | 1.25 | 4 | 0 | 100-101 |
| 90 | 7.5 | 2.5 | 4 | 0 | |
| 85 | 11.25 | 3.75 | 4 | 0 | 110-111 |
| 80 | 15 | 5 | 4 | 0 | |
| 90 | 10 | | 4 | 0 | 93-94 |
| 80 | 20 | | 4 | 0 | 103-104 |

Compatibility Evaluation of HFPO-Monoacrylates with Hydrocarbon Multi-Functional Acrylates and Mixtures of Hydrocarbon Multi-Functional Acrylates with Perfluoropolyether Urethane Multiacrylates MEK solutions of the mixtures shown in Table 15 were prepared at 30% solids. After thoroughly mixing the desired components at the ratios shown, approximately 3 ml of each soln was deposited onto a glass microscope slide and the solvent was allowed to evaporate over 16 hrs. The compatibility of the mixtures were than noted as either incompatible or compatible. An "Incompatible" observation was noted when the dried, uncured 100% solids mixture was either hazy or showed clear phase separations such as "oil-water type"

phase separation behavior. Compatible mixtures were observed to be clear or transparent with no visible detection of a second phase in the mixture. The mixtures were further diluted to 1.25% solids with MEK and 4% Darocur 1173 photoinitiator based on the solid content of the solution was added to the mixtures. An approximate 40 nm coating of each of these solutions was prepared on the substrate S1 by the use of a #2.5 Meyer Rod. The coatings were allowed to dry at room temperature and were cured at 10 fpm, 2-passes by use of Fusion Systems UV processor Model LCS BQ, The UV system was equipped with a Fusion Systems 500 w Light-Hammer model LH6 PS and used a H Bulb as the UV source. The cure chamber was flushed continuously with a positive nitrogen flow of approximately 20 psi. Contact angles were measured as described elsewhere in this application.

TABLE 15

Formulations used in Compatibility Studies of HFPO-urethanes, Non-urethane HFPO-monoacrylates and Hydrocarbon Multifunctional Acrylates.

| Sample | wt % TMPTA | wt % HFPO Urethane Acrylate | HFPO Acrylate | Type of Acrylate | wt % F | Static Water Contact Angle 40 nm | Compatibility at 100% Solids |
|---|---|---|---|---|---|---|---|
| 15-1  | 97 | 0  | 3  | 31a  | 1.85 | 104 | incompatible |
| 15-2  | 97 | 0  | 3  | 31b  | 1.74 | 96  | incompatible |
| 15-3  | 97 | 0  | 3  | 31c  | 1.72 | 101 | incompatible |
| 15-4  | 97 | 0  | 3  | 31d  | 1.81 | 102 | incompatible |
| 15-5  | 90 | 0  | 10 | 31a  | 6.17 | 103 | incompatible |
| 15-6  | 90 | 0  | 10 | 31b  | 5.8  | 102 | incompatible |
| 15-7  | 90 | 0  | 10 | 31c  | 5.73 | 99  | incompatible |
| 15-8  | 90 | 0  | 10 | 31d  | 6.02 | 101 | incompatible |
| 15-9  | 87 | 10 | 3  | 31a  | 3.41 | 101 | compatible |
| 15-10 | 87 | 10 | 3  | 31b  | 3.3  | 100 | compatible |
| 15-11 | 87 | 10 | 3  | 31c  | 3.28 | 98  | compatible |
| 15-12 | 87 | 10 | 3  | 31d  | 3.37 | 102 | compatible |
| 15-13 | 85 | 10 | 5  | 31a  | 4.65 | 106 | compatible |
| 15-14 | 85 | 10 | 5  | 31b  | 4.46 | 101 | compatible |
| 15-15 | 85 | 10 | 5  | 31c  | 4.42 | 101 | compatible |
| 15-16 | 85 | 10 | 5  | 31d  | 4.57 | 104 | compatible |
| 15-17 | 97 | 3  | 0  | None | 0.47 | 65  | compatible |
| 15-18 | 90 | 10 | 0  | None | 1.56 | 94  | compatible |
| 15-19 | 80 | 20 | 0  | None | 3.12 | 104 | compatible |

Compatibility Studies of Perfluoropolyether Urethane Multiacrylates with Perfluoropolyether (PFPE) Multiacrylates, Hydrocarbon Multi-Functional Acrylates and Nonurethane PFPE Multiacrylates MEK solutions of the mixtures shown in Table 16 were prepared at 30% solids. After mixing the desired components thoroughly, approximately 3 ml of each soln was deposited onto a glass microscope slide and the solvent was allowed to evaporate. After 16 hrs, the compatibility of the mixtures was noted according to the criteria described for Table 15.

TABLE 16

| Sample | SR 351 | HFPO-Urethane #6 | PFPE multiacrylates at 3 wt % | Calc wt % F in Coating | Compatibility |
|---|---|---|---|---|---|
| 16-1  | 87 | 10 | HFPO Prep 25  | 3.32 | compatible |
| 16-2  | 87 | 10 | HFPO Prep 28  | 3.31 | compatible |
| 16-3  | 87 | 10 | HFPO Prep 29  | 3.06 | compatible |
| 16-4  | 87 | 10 | LTM Diacrylate| 3.36 | compatible |
| 16-5  | 87 | 10 | CN 4000       | 3.21 | compatible |
| 16-6  | 97 | 0  | HFPO Prep 25  | 1.76 | incompatible |
| 16-7  | 97 | 0  | HFPO Prep 28  | 1.75 | incompatible |
| 16-8  | 97 | 0  | HFPO Prep 29  | 1.50 | incompatible |
| 16-9  | 97 | 0  | LTM Diacrylate| 1.80 | incompatible |
| 16-10 | 97 | 0  | CN 4000       | 1.65 | incompatible |

Each formulation also contained 4 wt % Darocur 1173 photoinitiator

Formulations described in Table 16, were coated on S-1 at approximately 40 nm coating weight using the same method as described in Table 15. Contact angle measurements and durability were determined as previously described. The results are shown in Table 17.

TABLE 17

Test Results of Formulations of Table 16

| Sample | PFPE Description | Durability Sand test 300 rpms/15 min/ 50 g sand | Static Water Contact Angle Before Durability Testing |
|---|---|---|---|
| 16-1  | HFPO Prep 25   | Yes          | 108.3 |
| 16-2  | HFPO Prep 28   | Yes          | 105.4 |
| 16-3  | HFPO Prep 29   | Yes          | 105.6 |
| 16-4  | LTM Diacrylate | Yes          | 105.7 |
| 16-5  | CN 4000        | Yes          | 106.2 |
| 16-6  | HFPO Prep 25   | Yes-partial  | 83.6  |
| 16-7  | HFPO Prep 28   | No           | 97.4  |
| 16-8  | HFPO Prep 29   | No           | 77    |
| 16-9  | LTM Diacrylate | No           | 70.6  |
| 16-10 | CN 4000        | No           | 98.2  |

Coating formulations comprising the multifunctional PFPE acrylates (Preps 25, 28, 29), LTM diacrylate, and CN4000, were prepared at constant weight percent fluorine by mixing with TMPTA. These compositions were compared to Coating Formulation #9 of Table 15, to exemplify the utility of the HFPO—U acrylate as a compatibilizer for either PFPE Multifunctional acrylate or HFPO-monoacrylates. The compositions are shown in Table 18 and the surface contact angles and durabilities are shown in Table 19.

TABLE 18

Formulations for Perfluoropolymer Polyethers Multifunctional Acrylates without HFPO-Urethane Formulated to Similar wt-% Fluorine

| Sample | wt % TMPTA | PFPE | Type of PFPE | Darocur | wt % F | Coating Quality |
|---|---|---|---|---|---|---|
| 18-1 | 93.5 | 6.5 | HFPO Prep 25 | 4 | 3.80 | Poor-dewets/streaks |
| 18-2 | 94 | 6 | HFPO Prep 28 | 4 | 3.47 | Good |
| 18-3 | 93.2 | 6.8 | HFPO Prep 29 | 4 | 3.40 | Good |
| 18-4 | 94.2 | 5.8 | LTM Diacrylate | 4 | 3.47 | Poor-dewets/streaks |
| 18-5 | 93.7 | 6.3 | CN 4000 | 4 | 3.47 | Good |
| 16-9 | | | | | 3.41 | Good |

TABLE 19

40 nm Coatings of Formulations of Table 18 (coated as described for Table 15)

| 1.25% solids, ~40 nm thickness Sample | Water Static | Coating quality 40 nm | Ink repellency IR loss after sand test 300 rpms/15 min/50 g sand |
|---|---|---|---|
| 18-1 | 108.9 | Good | 80% |
| 18-2 | 101.6 | Good | 80% |
| 18-3 | 95.8 | Good | 100% |
| 18-4 | 98.6 | Good | 35% |
| 18-5 | 100.1 | Good | 41% |
| 16-9 | 108.7 | Good | 0% |

While the invention has been described in terms of preferred embodiments, it will be understood, of course, that the invention is not limited thereto since modifications may be made by those skilled in the art, particularly in light of the foregoing teachings.

What is claimed is:

1. A fluorocarbon- and urethane-(meth)acryl-containing composition comprising a perfluoropolyether urethane having a perfluoropolyether moiety and a multi-(meth)acryl terminal group and having the formula: $_n(_p(A)QO(O)CHN)$—$R_i$—$(NHC(O)XQR_f)_m$;
   wherein
   $R_i$ is the residue of a multi-isocyanate;
   X is O, S or NR, wherein R is H or an alkyl group having 1 to 4 carbon;
   $R_f$ is a monovalent perfluoropolyether moiety comprising groups of the formula $F(R_{fc}O)_xC_dF_{2d}$-, wherein each $R_{fc}$ is independently a fluorinated alkylene group having from 1 to 6 carbon atoms,
   each x is an integer greater than or equal to 2, and wherein d is an integer from 1 to 6;
   each Q is independently a connecting group having a valency of at least 2;
   A is a (meth)acryl functional group —$XC(O)C(R_2)$=$CH_2$ wherein $R_2$ is an alkyl group of 1 to 4 carbon atoms or H or F;
   m is at least 1; n is at least 1; p is 2 to 6; m+n is 2 to 10; wherein the perfluoropolyether urethane further comprises at least one unit attached to the $R_i$ unit selected from
—(NHC(O)XQG),
—(NCO),
$R_f(O)(XC(O)NH)_y$—,
—(NHC(O)XQD(QXC(O)NH)_u$—,
-$D_1(QXC(O)NH)_y$,
—(NHC(O)OQ(A)_tQ_1Q(A)_tOC(O)NH)—, and
$(NHC(O)XQ$-$R_{f2}(QXC(O)NH)_u$—,
wherein
G is selected from the group consisting of alkyl, aryl, alkaryl, aralkyl, fluoroalkyl, perfluoroalkyl;
or a reactive group selected from (meth)acryl groups, vinyl groups, allyl groups and —$Si(OR_3)_3$ groups, where $R_3$ is a lower alkyl of 1 to 4 carbon atoms;
D is selected from the group consisting of alkylene, arylene, alkarylene, fluoroalkylene, perfluoroalkylene, and aralkylene; or said D group further containing heteroatoms selected from O, N, and S;
$D_1$ is selected from the group consisting of alkyl, aryl, alkaryl, fluoroalkyl, perfluoroalkyl, and aralkyl, or said $D_1$ group further containing heteroatoms selected from O, N, and S;
$Q_1$ are each independently a connecting group of valency at least 2;
$R_{f2}$ is a multi-valent perfluoropolyether moiety having the formula $Y((R_{fc1}O)_xC_{d1}F_{2d1})_b$,
wherein each $R_{fc1}$ is independently selected from: —CF(CF_3)CF_2—, —$CF_2CF_2CF_2$—, and $(CH_2C(CH_3)(CH_2OCH_2CF_3)CH_2$—$)_{aa}$ where aa is 2 or greater; each x is independently an integer greater than or equal to 2, d1 is an integer from 0 to 6; Y represents a polyvalent organic group or covalent bond having a valence of b, and b represents an integer greater than or equal to 2;
y is independently 2 or greater;
u is independently 1 to 3; and
t is 1-6.

2. The composition of claim 1 with the proviso that when X is O, Q is not methylene.

3. The composition of claim 1 wherein X is S or NR.

4. The composition of claim 1 wherein Q is an alkylene having at least two carbon atoms.

5. The composition of claim 1 wherein Q is a straight chain, branched chain, or cycle-containing connecting group.

6. The composition of claim 5 wherein Q is selected from the group consisting of a covalent bond; an arylene; an aralkylene; and alkarylene.

7. The composition of claim 5 wherein Q comprises a heteroatom selected from O, N, and S.

8. The composition of claim 5 wherein Q comprises a heteroatom-containing functional group selected from carbonyl and sulfonyl.

9. The composition of claim 5 wherein Q is a straight chain alkylene group comprising heteroatoms selected from O, N, S; a heteroatom-containing functional group selected from carbonyl and sulfonyl, and combinations thereof.

10. The composition of claim 5 wherein Q is branched chain or cycle-containing alkylene group.

11. The composition of claim 1 wherein Q is a nitrogen containing group.

12. The composition of claim 11 wherein Q contains an amide group.

13. The composition of claim 1 wherein the composition further comprises ethylene oxide repeat units.

14. The composition of claim 1 wherein n is 2.

15. The composition of claim 1 wherein the perfluoropolyether urethane is the reaction product of a biuret of HDI.

16. The composition of claim 1 wherein G further comprises O, N, S, or a combination thereof.

* * * * *

UNITED STATES PATENT AND TRADEMARK OFFICE
CERTIFICATE OF CORRECTION

PATENT NO. : 8,729,211 B2
APPLICATION NO. : 13/908102
DATED : May 20, 2014
INVENTOR(S) : Thomas Klun It is certified that error appears in the above-identified patent and that said Letters Patent is hereby corrected as shown below:

In the Specification

Column 10
Line 31, Delete "$F_{2d1})_b$" and insert -- $F_{2d1})b$, --, therefor.
Line 41, Delete "R." and insert -- $R_i$. --, therefor.

Column 12
Line 20, Delete "—$CF_2$ $CF_2O(CF_2CF_2CF_2O)_nCF_2CF_2$—," and insert
-- —$CF_2CF_2O(CF_2CF_2CF_2O)_nCF_2CF_2$—, --, therefor.

Column 14
Line 23, Delete "$CH=CH_2$" and insert -- $CH=CH_2$. --, therefor.

Column 20
Line 29, Delete "minimized" and insert -- minimized. --, therefor.

Column 24
Line 31, Delete "SR444c," and insert -- SR444C, --, therefor.

Column 28
Line 60, Delete "SR444c." and insert -- SR444C. --, therefor.

Column 29
Line 47, Delete "$CH_2C(=O)$" and insert -- $CH_2OC(=O)$ --, therefor.
Line 59, Delete "$CH_2C(=O)$" and insert -- $CH_2OC(=O)$ --, therefor.

Column 30
Line 27, Delete "$CF_2$ $O)_c$" and insert -- $CF_2O)_c$ -- therefor

Signed and Sealed this
Thirty-first Day of March, 2015

Michelle K. Lee
*Director of the United States Patent and Trademark Office*

CERTIFICATE OF CORRECTION (continued)
U.S. Pat. No. 8,729,211 B2

In the Claims

Column 42
Line 3, In Claim 1, delete "(O)" and insert -- (Q) --, therefor.